United States Patent [19]

Lyga

[11] Patent Number: 4,766,233

[45] Date of Patent: Aug. 23, 1988

[54] HERBICIDAL 2-ARYL-1,2,4-TRIAZINE-3,5(2H,4H)-DIONES AND SULFUR ANALOGS THEREOF

[75] Inventor: John W. Lyga, Basking Ridge, N.J.

[73] Assignee: FMC Corporation, Philadelphia, Pa.

[21] Appl. No.: 807,790

[22] PCT Filed: Jun. 3, 1985

[86] PCT No.: PCT/US85/01041

§ 371 Date: Jul. 2, 1985

§ 102(e) Date: Jul. 2, 1985

[87] PCT Pub. No.: WO86/00072

PCT Pub. Date: Jan. 3, 1986

Related U.S. Application Data

[63] Continuation-in-part of Ser. No. 755,749, Jul. 2, 1985, abandoned.

[51] Int. Cl.[4] .................................... C01C 79/46

[52] U.S. Cl. .................................... 560/22; 560/13; 560/25; 71/88; 71/94; 71/95; 71/98; 71/103; 71/105; 71/111; 544/182; 558/255; 558/389; 558/417; 548/556

[58] Field of Search .................... 560/22, 25, 16, 22, 560/34; 558/391; 544/182; 71/93, 103

[56] References Cited

U.S. PATENT DOCUMENTS

| | | | |
|---|---|---|---|
| 3,206,450 | 9/1965 | Kelly | 560/34 |
| 3,632,574 | 1/1972 | Yamamoto et al. | 560/34 |
| 3,641,098 | 2/1972 | Buchel et al. | 560/34 |
| 3,883,527 | 7/1975 | Brennan | 260/248 |
| 3,907,543 | 9/1975 | Dickore et al. | 71/93 |

Foreign Patent Documents

| | | |
|---|---|---|
| 3016304 | 11/1980 | Fed. Rep. of Germany . |
| 0011693 | 12/1980 | Fed. Rep. of Germany . |

OTHER PUBLICATIONS

Whitely et al., Journal of the Chemical Society, 1927, Pt. 1, pp. 521–528.

Miller et al., I, J. Med. Chem. 1981, 24, 1337–1342.

Miller et al., II, J. Med. Chem. 1979, 22, 1483–1487.

*Primary Examiner*—Glennon H. Hollrah
*Assistant Examiner*—A. Owens
*Attorney, Agent, or Firm*—Robert M. Kennedy; H. Robinson Ertelt; William Schmonsees

[57] ABSTRACT

Herbicidal utility for 2-aryl-1,2,4-triazine-3,5(2H,4H)-diones and sulfur analogs is disclosed and exemplified. Many of the disclosed compounds are novel. Methods for preparing the herbicidal compounds and intermediates therefor are also disclosed.

4 Claims, No Drawings

HERBICIDAL 2-ARYL-1,2,4-TRIAZINE-3,5(2H,4H)-DIONES AND SULFUR ANALOGS THEREOF

This application is a continuation-in-part of application Ser. No. 755,749, filed July 2, 1985, now abandoned.

The invention described in this application pertains to weed control in agriculture, horticulture, and other fields where there is a desire to control unwanted plant growth. More specifically, the present application describes herbicidal 2-aryl-1,2,4-triazine-3,5(2H,4H)-diones, sulfur analogs thereof, compositions of them, methods of preparing them, and methods for preventing or destroying undesired plant growth by preemergence or postemergence application of the herbicidal compositions to the locus where control is desired. The present compounds may be used to effectively control a variety of both grassy and broadleaf plant species. The present invention is particularly useful in agriculture, as a number of the compounds described herein show a selectivity favorable to soybean, corn, cotton, wheat, rice, or other crops at application levels which prevent the growth of or destroy a variety of weeds.

1,2,4-Triazine-3,5(2H,4H)-diones as a class are generally associated with the pharmaceutical or animal health arts and are commonly referred to therein as 6-azauracils. Such compounds, however, are relatively unknown in the herbicide art. In particular, there does not appear to be any disclosure of 2-aryltriazinediones in the art. Herbicidal activity is disclosed in German Offenlegungsschrift No. 3,016,304 for optionally substituted triazinediones having the formula

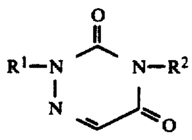

where $R^1$ is hydrogen, hydroxymethyl or an ester derivative thereof such as a benzoic acid ester, optionally substituted aminomethyl, optionally halo-substituted 2-tetrahydrofuranyl, 2-(2H,5H)dihydrofuranyl, or 2-tetrahydropyranyl, and $R^2$ is hydrogen, an optionally substituted aminomethyl, optionally halo-substituted 2-tetrahydrofuranyl, or 2-tetrahydropyranyl, with certain provisos.

European Published Patent Application No. 0 011 693 of 1979 refers to phenyltriazinediones having a $-NHSO_2CF_3$ substituent on the phenyl group. The compounds of the present invention do not require such a substituent for their herbicidal effects.

It has now been discovered that 2-aryl-1,2,4-triazine-3,5-(2H,4H)-diones and the corresponding sulfur analogs have herbicidal properties and may be used effectively either preemergently or postemergently for herbicidal purposes.

The herbicidal compounds of this invention have the formula

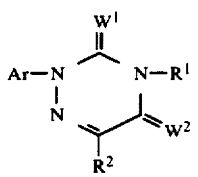

where Ar is an aryl radical, preferably a ring-substituted aryl radical. For instance it may have a benzene ring such as the radical indicated by the following formula

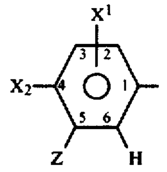

wherein $X^1$ may be for instance hydrogen or halogen, preferably fluorine or chlorine, the halogen atom advantageously being positioned at the C-2 carbon atom of the phenyl ring;

$X^2$ may be hydrogen, halogen such as fluorine, chlorine, or bromine, alkyl of 1 to 6 (preferably 1 to 4) carbon atoms, particularly methyl, haloalkyl of 1 to 5 carbon atoms, for example, trifluoromethyl, alkoxy of 1 to 6 (preferably 1 to 4 ) carbon atoms, or phenoxy or phenylmethoxy which may be ring substituted with halogen or alkyl or alkoxy of 1 to 4 carbon atoms;

Z may be hydrogen or, preferably, a substituent or group selected from fluorine, chlorine, bromine, iodine, cyano, nitro, amino, alkoxycarbonylamino of 1 to 6 (preferably 1 to 4) alkyl carbon atoms, di(alkylcarbonyl-)amino in which each alkyl is of 1 to 6 (preferably 1 to 4) carbon atoms, hydroxysulfonyl, alkyl of 1 to 6 (preferably 1 to 4) carbon atoms, haloalkyl of 1 to 5 carbon atoms, $-QR$, $-CO-R^6$, $-S(O)_mR^8$, $-Q^2R^9$, $-OSO_2R^{10}$, $-NHN{=}CR^{11}R^{12}$, and $-Q-CR^3R^4-(CH_2)_n-CO-Q^1-R^5$.

For $Z{=}-QR$, Q may be O, S, or $NR^7$; $R^7$ may be hydrogen or alkyl of 1 to 6 (preferably 1 to 4) carbon atoms; and R may be alkyl of 1 to 6 (preferably 1 to 4) carbon atoms, which may be substituted with cycloalkyl of 3 to 7 carbon atoms (for example, methyl, 1-methylethyl, or cyclohexylmethyl), cycloalkyl of 3 to 7 (preferably 5 or 6) carbon atoms which may be substituted with alkyl of 1 to 6 carbon atoms (for example, cyclopentyl or methylcyclopropyl), alkoxyalkyl of 2 to 8 (preferably 2 to 4) carbon atoms (for example, ethoxymethyl), alkoxyalkoxyalkyl of 3 to 8 (preferably 3 to 5) carbon atoms (for example, 2-methoxyethoxymethyl), alkylthioalkyl of 2 to 8 (preferably 2 to 4) carbon atoms or the sulfinyl or sulfonyl derivative thereof, tri(alkyl of 1 to 4 carbon atoms)silyl(alkyl of 1 to 4 carbon atoms) such as trimethylsilylmethyl, cyanoalkyl of 1 to 5 (preferably 1 to 3) alkyl carbon atoms such as cyanomethyl or 2-cyanoethyl, alkenyl of 2 to 5 (preferably 3 to 5) carbon atoms such as 2-propenyl, alkynyl of 2 to 5 (preferably 3 to 5) carbon atoms such as 2-propynyl, haloalkyl of 1 to 5 (preferably 1 to 3) carbon atoms especially a fluoroalkyl, haloalkenyl of 2 to 5 (preferably 3 to 5) carbon atoms, haloalkynyl of 2 to 5 (preferably 3 to 5) carbon atoms such as 3-bromo-2-propynyl, alkylcarbonyl of 1 to 6 (preferably 1 to 4) alkyl carbon atoms such as acetyl, or dialkylaminocarbonyl or dialkylaminothiocarbonyl in which each alkyl is of 1 to 6 (preferably 1 to 4) carbon atoms.

The compounds in which Z=—QR, especially where $X^1$ is 2-F and $X^2$ is Cl or Br, form a preferred embodiment of the invention; particularly where Q is sulfur, more particularly where Q is oxygen. Frequently, R will be selected from among alkyl, cyanoalkyl, alkynyl, haloalkynyl, and alkoxyalkynyl. Typical such R groups include, for example, 1-methylethyl, cyanomethyl, 2-propynyl, 3-bromo-2-propynyl, and methoxymethyl. Preferably R will be 1-methylethyl or, especially, 2-propynyl or methoxymethyl.

For Z=—CO—$R^6$, $R^6$ may be hydroxy, alkoxy or alkylthio of 1 to 6 (preferably 1 to 4) carbon atoms such as methoxy or methylthio, alkoxyalkoxy of 2 to 6 (preferably 2 to 4) carbon atoms (for example, 2-methoxyethoxy), amino, or alkylamino or dialkyamino wherein each alkyl is of 1 to 6 (preferably 1 to 4) carbon atoms and may be substituted with alkoxy of 1 to 4 carbon atoms (for example, methylamino, dimethylamino, or methyl(2-methoxyethyl)amino). For example, Z, defined as —CO—$R^6$, may be $CO_2H$, $CO_2$alkyl, CO—S-alkyl, $CO_2$alkyl-O-alkyl, $CONH_2$, or CONH-alkyl or $CON(alkyl)_2$ in which any alkyl may be substituted with alkoxy. Compounds in which Z is —CO—$R^6$, especially where $X^1$ is 2-F and $X^2$ is Cl or Br, form a preferred embodiment of the invention.

For Z=—$S(O)_mR^8$, m may be 1 or 2 and $R^8$ may be alkyl of 1 to 6 (preferably 1 to 4) carbon atoms or alkenyl or alkynyl of 2 to 5 (preferably 3 to 5) carbon atoms. For example, Z may be —SO—$CH_3$, —$SO_2CH(CH_3)_2$, —$SO_2CH_2CH{=}CH_2$, or —SO—$CH_2C{\equiv}CH$.

For Z=—$Q^2R^9$, $Q^2$ may be sulfur or, preferably, oxygen, and $R^9$ may be a 5- or 6-membered ring heterocyclic group of 1 or 2 same or different (preferably the same) heteroatoms selected from O, S (including the S-oxide and S-dioxide), and N or an alkyl radical of 1 to 5 (preferably 1 to 3) carbon atoms substituted with said heterocyclic group. $R^9$ will frequently be (a) an optionally substituted and optionally benzene-adjoined nitrogen-containing heterocycle or an alkyl radical of 1 to 5 carbon atoms substituted with said heterocycle;

(b) an aromatic, optionally substituted and optionally benzene-adjoined, oxygen- or sulfur-containing heterocycle or an alkyl group of 1 to 5 carbon atoms substituted therewith; or, advantageously, (c) a non-aromatic, optionally substituted and optionally benzene-adjoined, oxygen- or sulfur-containing heterocycle or an alkyl group of 1 to 5 carbon atoms substituted therewith.

Examples of $R^9$ groups include 1-methyl-3-pyrrolidinyl, furfuryl, 2-thienylmethyl, 3-tetrahydrofuranyl, tetrahydrofurfuryl, tetrahydropyran-2-ylmethyl, 1,3-dioxolan-2-ylmethyl, 2-(1,3-dioxolan-2-yl)ethyl, 2,2-dimethyl-1,3-dioxolan-4-ylmethyl, 3-(2-methyl-1,3-dioxolan-2-yl)propyl, 1,3-dioxan-4-ylmethyl, 1,4-benzodioxan-2-ylmethyl, tetrahydro-4H-pyran-4-yl, 5,6-dihydro-2H-pyran-3-ylmethyl, 2,2-dimethyl-1,3-dithiolan-4-ylmethyl, tetrahydro-4H-thiopyran-4-yl, tetrahydrothien-3-yl, 1-oxotetrahydrothien-3-yl, 1,1-dioxotetrahydrothien-3-yl, 2,2-dimethyl-1,1,3,3-tetraoxo-1,3-dithiolan-4-ylmethyl, 1,1-dioxotetrahydro-4H-thiopyran-4-yl, and 1,3-oxothiolan-2-ylmethyl.

For Z=—$OSO_2R^{10}$, $R^{10}$ may be alkyl of 1 to 6(preferably 1 to 4) carbon atoms (which may be substituted with halogen, cyano, alkoxy or alkylthio of 1 to 4 carbon atoms, or alkylamino or dialkylamino in which alkyl is of 1 to 4 carbon atoms), phenyl, or alkylamino or dialkylamino in which alkyl is of 1 to 4 carbon atoms. Examples of such Z substituents include phenylsulfonyloxy, methylsulfonyloxy, ethylsulfonyloxy, propylsulfonyloxy, butylsulfonyloxy, 1-methylethylsulfonyloxy, 1-methylpropylsulfonyloxy, 2-methylpropylsulfonyloxy, 3-methylbutylsulfonyloxy, chloromethylsulfonyloxy, 3-chloropropylsulfonyloxy, trifluoromethylsulfonyloxy, methylaminosulfonyloxy, dimethylaminosulfonyloxy, dimethylaminoethylsulfonyloxy, 2-methoxyethylsulfonyloxy, 2-ethoxyethylsulfonyloxy, and cyanomethylsulfonyloxy.

For Z=—NHN=$C(R^{11})(R^{12})$, one of $R^{11}$ and $R^{12}$ may be hydrogen or alkyl of 1 to 4 carbon atoms and the other may be alkyl of 1 to 4 carbon atoms, or $C(R^{11})(R^{12})$ taken as a unit may be cycloalkyl of 3 to 7 (preferably 5 to 7) carbon atoms. For example, Z may be $NHN{=}C(CH_3)_2$, $NHN{=}CHCH_2CH_3$, $NHN{=}C(CH_3)(C_2H_5)$,

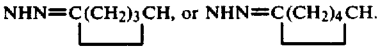

For

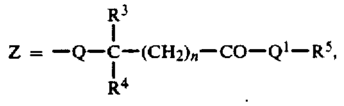

n may be 0 to 2, preferably 0; $R^3$ may be hydrogen or alkyl of 1 to 4 carbon atoms; $R^4$ may be hydrogen, alkyl of 1 to 4 carbon atoms, or alkoxy of 1 to 4 carbon atoms; Q and $Q^1$ may be independently O, S or $NR^7$ in which $R^7$ is hydrogen or alkyl of 1 to 6 (preferably 1 to 4) carbon atoms; and $R^5$ may be hydrogen, alkyl of 1 to 6 (preferably 1 to 4) carbon atoms which may be substituted with cycloalkyl of 3 to 7 carbon atoms (for example, methyl, cyclopropylmethyl, cyclopentylmethyl, or cyclohexylmethyl), cycloalkyl of 3 to 7 carbon atoms which may be substituted with alkyl of 1 to 4 carbon atoms (for example, methylcyclopropyl, cyclopentyl, cyclohexyl, 2-methylcyclohexyl, or cycloheptyl), alkoxyalkyl or alkylthioalkyl of 2 to 6 carbon atoms, haloalkyl of 1 to 5 carbon atoms (especially fluoroalkyl or chloroalkyl), alkenyl of 2 to 5 carbon atoms such as 2-propenyl, cycloalkenyl of 5 to 7 carbon atoms which may be substituted with alkyl of 1 to 4 carbon atoms (for example, 2-cyclohexenyl), cycloalkenylalkyl of 6 to 10 carbon atoms (for example, 3-cyclohexenylmethyl), phenyl or phenylmethyl (each of which may be ring-substituted with fluorine, chlorine, bromine, or alkyl, alkoxy, or alkylthio of 1 to 4 carbon atoms), cyanoalkyl of 1 to 5 alkyl carbon atoms such as cyanomethyl, alkynyl of 2 to 5 carbon atoms such as 2-propynyl, alkylimino of 1 to 6 (preferably 1 to 4) carbon atoms which may be substituted with cycloalkyl of 3 to 7 carbon atoms, or cycloalkylimino of 5 to 7 carbon atoms which may be substituted with alkyl of 1 to 4 carbon atoms; or $Q^1$ and $R^5$ may together represent a phenylsulfonylamino group in which the phenyl is unsubstituted or substituted with halogen such as fluorine, chlorine, or bromine, alkyl of 1 to 4 carbon atoms, alkoxy of 1 to 4 carbon atoms, or alkoxycarbonyl of 1 to 4 alkyl carbon atoms.

This subgenus, especially where $X^1$ is 2-F and $X^2$ is Cl or Br, forms a preferred embodiment of the invention;

particularly where n is 0 and one of $R^3$ and $R^4$ is H and the other H, $CH_3$, $C_2H_5$, $OCH_3$, or $OC_2H_5$. Where Q or $Q^1$ is $NR^7$, $R^7$ is preferably H. Examaples of Z substituents where Q is $NR^7$ include those of the formula $-NHCH_2CO_2R^5$ and $-NHCH(CH_3)CO_2R^5$ where $R^5$ is methyl, ethyl, propyl, butyl, 2-methoxyethyl, 2-propoxyethyl, 2-cyanoethyl, 2,3-dichloropropyl, 2,2-dichloroethyl, cyclopentylmethyl, cyclopentyl, 1-methylethyl, 1-ethylpropyl, or 1-methylpropyl.

Thus, Z may be H or a substituent or group such as F, Cl, Br, I, $NO_2$, $NH_2$, CN, $SO_3H$, alkyl haloalkyl, OR, SR, $NR^7R$, $NHCO_2$-alkyl, N(CO-alkyl)$_2$, CO—$R^6$, SO—$R^8$ , $SO_2$—$R^8$, $OR^9$, $SR^9$, $OSO_2R^{10}$, NHN=$CR^{11}R^{12}$, O—$CR^3R^4$—$CO_2R^5$, O—$CR^3R^4$—CO—$SR^5$, O—$CR^3R^4$—CO—$NR^7R^5$, S—$CR^3R^4$—$CO_2R^5$, S—$CR^3R^4$—CO—$SR^5$, S—$CR^3R^4$—CO—$NR^7R^5$, $NR^7$—$CR^3R^4$—$CO_2R^5$, $NR^7$—$CR^3R^4$—CO—$SR^5$, or $NR^7$—$CR^3R^4$—CO—$NR^7R^5$.

The aryl moiety of the present aryltriazinediones may be a heteroaromatic radical such as a furyl, thienyl, pyridyl, pyrimidyl, oxazolyl, pyrrolyl, isoxazolyl, thiazolyl, or isothiazolyl radical which may carry one or more substituents, for example, halogen and/or alkyl or alkoxy of 1 to 6 (preferably 1 to 4) carbon atoms. Preferably, however, the aryl moiety will be a phenyl radical, particularly a halophenyl radical, more particularly a dihalophenyl radical.

In a preferred embodiment for herbicidal activity, the present compounds will have the formula:

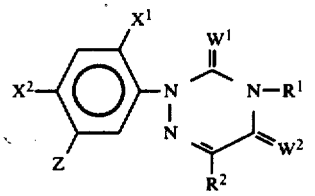

I in which $X^1$ and $X^2$ are both halogen atoms and Z is as defined above. $X^1$ is preferably chlorine or, especially, fluorine. $X^2$ is preferably chlorine or bromine.

With respect to the triazinedione portion of the molecule, $R^1$ may be alkyl of 1 to 6 (preferably 1 to 4) carbon atoms; haloalkyl of 1 to 5 (preferably 1 to 3) carbon atoms; cyanoalkyl of 1 to 5 (preferably 1 to 3) alkyl carbon atoms; alkenyl or alkynyl of 2 to 5 (preferably 3 to 5) carbon atoms; alkoxyalkyl, alkylthioalkyl, alkylsulfinylalkyl, or alkylsulfonylalkyl of 2 to 5 (preferably 2 to 4) carbon atoms; or amino. $R^1$ will frequently and conveniently be a lower alkyl group such as methyl or ethyl, especially methyl. When $R^1$ is haloalkyl, the alkyl radical may be substituted with one or more same or different halogen atoms, preferably the same and preferably fluorine. Typical fluoroalkyl groups include fluoromethyl, difluoromethyl, 2-fluoroethyl, and 3-fluoropropyl. Examples of other $R^1$ substituents include cyanomethyl, amino, 2-propenyl, 2-propynyl, 2-methoxyethyl, methylthiomethyl, methylsulfinylmethyl, and methylsulfonylmethyl. In a preferred embodiment, $R^1$ is methyl or a fluoromethyl having 1 to 2 fluorine atoms, especially methyl.

$R^2$ may be hydrogen; halogen, especially fluorine, chlorine, or bromine; alkyl of 1 to 4 carbon atoms, especially methyl; haloalkyl of 1 to 4 carbon atoms, particularly a fluoroalkyl such as trifluoromethyl; cyanoalkyl of 1 to 4 alkyl carbon atoms such as cyanomethyl; alkenyl of 2 to 4 carbon atoms such as 2-propenyl; alkynyl of 2 to 4 carbon atoms such as 2-propynyl; alkoxyalkyl of 2 to 4 carbon atoms, for example, 2-methoxyethyl; amino; hydroxycarbonyl; or alkoxycarbonyl of 1 to 4 alkyl carbon atoms. Compounds in which $R^2$ is hydroxycarbonyl, while in themselves or as salts are generally herbicidal at high application rates, are more useful as intermediates (for the corresponding compounds in which $R^2$ is hydrogen) than as herbicides. In a preferred embodiment, $R^2$ is hydrogen or methyl, especially hydrogen.

The groups $W^1$ and $W^2$ are independently selected from oxygen and sulfur. Thus, $W^1$ and $W^2$ may both be oxygen or sulfur, $W^1$ may be oxygen and $W^2$ may be sulfur, or $W^1$ may be sulfur and $W^2$ may be oxygen. In a preferred embodiment $W^1$ and $W^2$ are both oxygen.

A preferred subgenus for high herbicidal activity comprises the compounds of the formula

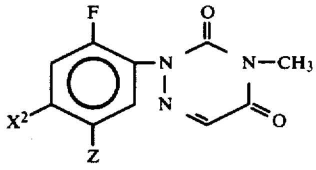

Ia in which $X^2$ is bromine or chlorine and Z is as defined above. Compounds in which the fluorine atom at C-2 of the phenyl ring is replaced by a chlorine atom and Z is other than hydrogen are also of particular interest.

It will be understood that any alkyl, alkenyl or alkynyl group herein may be straight chain or branched chain radicals. Thus, 1-methylethyl, 2-methyl-2-propenyl, and 1-methyl-2-propynyl are branched chain examples of alkyl, alkenyl, and alkynyl radicals respectively. Halogen may be fluorine, chlorine, bromine, or iodine. Haloalkyl radicals may have one or more same or different halogen atoms.

Any herbicidal compound of the present invention in which $R^2$ is $CO_2H$ or in which Z is or contains $SO_3H$ or $CO_2H$ may, of course, be converted into a salt such as a sodium, potassium, calcium, ammonium, magnesium, or mono-, di-, or tri($C_1$ to $C_4$ alkyl)ammonium salt which may also be used as an herbicide. Such salts are within the scope of the present invention.

A number of the compounds of the invention may more readily exist in hydrated form rather than as non-hydrated materials. It will be understood that the presence or absence of water of hydrating in the compounds is of no concern in determining the metes and bounds of the present invention.

The present compounds may be prepared by methods described in the literature or by methods analogous or similar thereto and within the skill of the art.

Many of the present compounds may be prepared as illustrated in the following chemical equations:

Method A: $R^2$=H or $CO_2H$

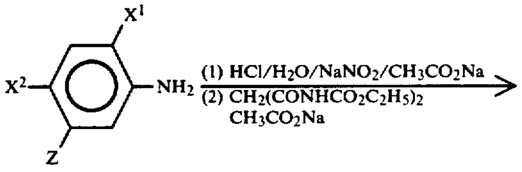

II

-continued

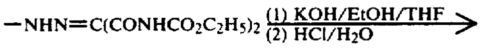

III

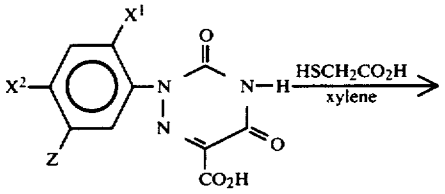

Ic

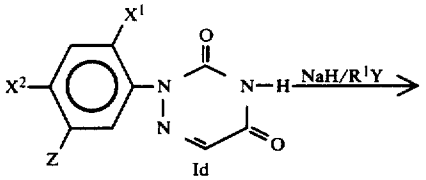

Id

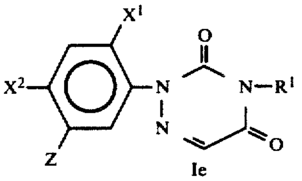

Ie

An appropriately substituted aniline, II, is treated first with aqueous hydrochloric acid, sodium acetate, and sodium nitrite, then with malonyldiurethane and sodium acetate to produce intermediate III. Compound III is cyclized by treatment first with ethanolic potassium hydroxide in tetrahydrofuran, then with aqueous hydrochloric acid to give the triazinedionecarboxylic acid Ic which is decarboxylated in the presence of mercaptoacetic acid and xylene to give the intermediate Compound Id. Treatment of Id with $R^1Y$, in which Y is a suitable leaving group, in the presence of a base gives the N-substituted triazinedione Ie.

Method B: $R^2$=H, alkyl

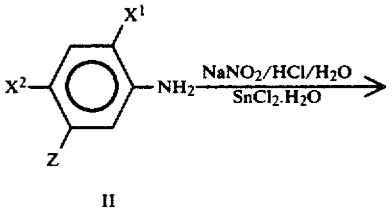

II

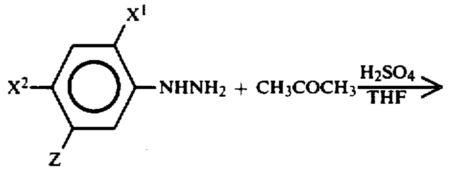

IV

-continued

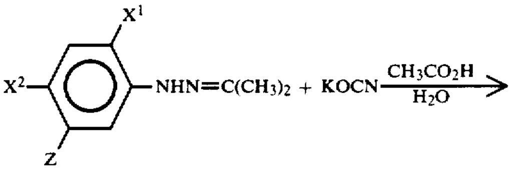

V

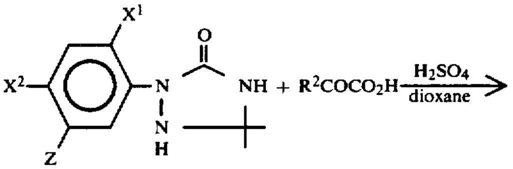

VI

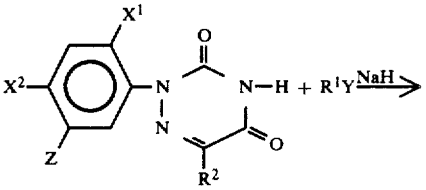

Ih

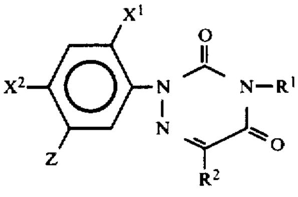

Ii

An appropriately substituted aniline is reacted with sodium nitrite and tin (II) chloride in aqueous hydrochloric acid to produce the corresponding hydrazine, Compound IV, which is converted to hydrazone V by treatment with acetone in sulfuric acid and tetrahydrofuran. Treatment of V with potassium cyanate in aqueous acetic acid gives triazolidinone VI which upon reaction with $R^2COCO_2H$ and sulfuric acid in dioxane produces triazinedione Ih. Reaction of Ih with $R^1Y$ wherein Y is a leaving group gives product Ii.

The methods illustrated above for producing Ie and Ii are generally applicable where the starting materials Compound II is readily available, either commercially or by preparation, and the substituent Z is stable under the conditions of the process. In some instances the desired Z substituent may be unstable under the conditions used in preparing the starting material II or in converting II into product Ie or Ii. In such cases or where it is otherwise not desirable or convenient to have the desired Z substituent in place at the outset, in Compound II, it may be advantageous to incorporate the desired Z group into the molecule further on in the process, for example, subsequent to the addition of the $R^1$ group.

For example, the products in which Z is $—OR^9$, $—OSO_2R^{10}$, $—OCR^3R^4CO—Q^1R^5$, or —OR (R is other than lower alkyl) may advantageously be prepared from Compound Ie (or Ii) in which Z is lower alkoxy or benzyloxy as illustrated in the following chemical equations:

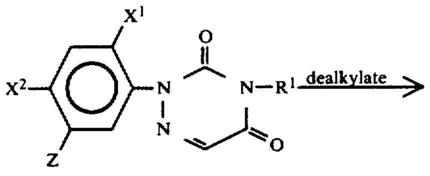

Ie (Z = O—alkyl or $OCH_2C_6H_5$)

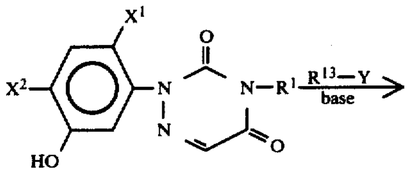

If

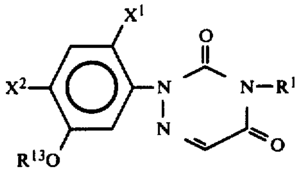

Ig

In the equations above $R^{13}$ represents the appropriate radical —$R^9$, —$SO_2R^{10}$, —$CR^3R^4$—CO—$Q^1R^5$, or —R and Y represents a leaving group. The phenolic intermediate If is readily prepared from the corresponding compound Ie in which Z is lower alkoxy or benzyloxy by treatment with an acidic reagent such as concentrated sulfuric acid, concentrated hydrobromic acid, or a mixture of hydrobromic and acetic acids to effect dealkylation, or, where Z is benzyloxy, by hydrogenolysis over palladium on charcoal ($H_2/Pd/C/C_2H_5OH$). Reaction of the 5-hydroxyphenyl intermediate If with the appropriate $R^9$—Y, $R^{10}$—$SO_2Y$, Y—$CR^3R^4$—CO—$Q^1R^5$, or R—Y, i.e., $R^{13}$—Y in the equation above, in the presence of a base gives product Ig.

Similarly, products corresponding to Ie or Ii in which Z is —$SR^{13}$, where $R^{13}$ has the meaning given above, may be prepared by treatment of the corresponding 5-mercaptophenyl compound with $R^{13}$—Y. The 5-mercaptophenyl compound may be prepared from the corresponding compound in which Z is hydrogen (Ie or Ii, Z=H) by the sequence of steps illustrated below:

$$\underset{(Z\,=\,H)}{\text{Ie}} \xrightarrow{HNO_3/H_2SO_4} \underset{\text{Ij}}{\text{5-}NO_2} \xrightarrow[C_2H_5OH]{H_2/PTO_2} \underset{\text{Ik}}{\text{5-}NH_2}$$

$$\text{Ik} \xrightarrow[(2)\ SO_2/CuCl]{(1)\ NaNO_2/HCl} \underset{\text{Il}}{\text{5-}SO_2Cl} \xrightarrow{Sn/HCl} \underset{\text{Im}}{\text{5-SH}}$$

Compound Ie in which Z is hydrogen may be nitrated to give the corresponding 5-nitro compound Ij, which may be reduced to give the corresponding 5-amino compound Ik. Compound Ik may be treated first with $NaNO_2$/HCl, then with $SO_2$/CuCl to give the 5-chlorosulfonyl compound Il which may be reduced with Sn/HCl to give the corresponding 5-mercapto compound Im.

As with the 5-OH and 5-SH intermediates, the 5-$NH_2$ compound, Ik, is an important intermediate which may be alkylated or acylated to introduce other Z substituents into the molecule. Compounds in which Z is alkoxycarbonylamino, di(alkylcarbonyl)amino, —$NR^7R$, or —$NR^7$—$CR^3R^4$—CO—$Q^1R^5$ may be prepared in this manner from the corresponding 5-$NH_2$ compound. An alternative method for introducing certain —NHR or —NH—$CR^3R^4$—CO—$Q^1R^5$ Z groups is illustrated in the equation below:

$$\underset{\text{Ik}}{\text{5-}NH_2} + CH_3COCH_3 \xrightarrow[THF]{BH_3-THF} \text{5-}NHCH(CH_3)_2$$

For example, Compounds 89 (Z=—$NHCH(CH_3)_2$), 206 (Z=—NH-cyclohexyl), and 232 (Z=—NH—$CH(CH_3)$—$CO_2C_2H_5$) shown in Table 1 below were prepared by condensing the corresponding 5-$NH_2$ compound with the appropriate ketone in the presence of borane in tetrahydrofuran.

The compound of formula Ie or Ii in which Z is —NHN=$CR^{11}R^{12}$ may also be produced from the corresponding compound in which Z is —$NH_2$ by reacting the 5-$NH_2$ compound with $NaNO_2$ and $SnCl_2$ in aqueous HCl to give the corresponding hydrazine (Ie, Z=—$NHNH_2$), followed by condensation with $R^{11}COR^{12}$.

The amino compounds (Ie or Ii, Z=—$NH_2$) may also be converted into the corresponding compounds in which Z is a halogen atom by treatment with nitrous acid under conditions which give a diazonium salt followed by treatment of the salt with the appropriate halogen reagent, for example, CuCl, CuBr, KI, or $HBF_4$.

The compounds of formula I in which $W^1$ or $W^2$ or both are sulfur may be prepared as follows. Compound Ie or Ii may be treated with one equivalent of $P_2S_5$ in pyridine to give the corresponding compound of formula I in which $W^2$ is sulfur; or Ie or Ii may be treated with at least two equivalents of $P_2S_5$ to produce the dithione derivative (I, $W^1=W^2=S$). Compound I in which $W^1$ is sulfur and $W^2$ is oxygen may be prepared by substituting KSCN for KOCN in Method B above to produce the triazolidinethione corresponding to the triazolidinone VI which may then be carried through the Method B process to give the 1,2,4-triazine-3-thione-5-one product.

The novel intermediates for the present herbicidal compounds are also part of the present invention, particularly compounds VII, VIII, IX, and X.

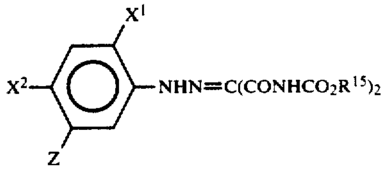

VII

-continued

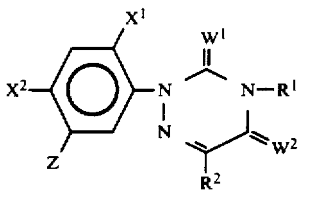

VIII ($R^1$ = H)
IX ($R^2$ = $CO_2H$)
X (Z = OH, SH, or $NH_2$)

In each of the compounds above, $X^1$, $X^2$, $W^1$, and $W^2$ are as defined above. Preferably $X^1$ and $X^2$ are both halogen, especially fluorine, chlorine, or bromine. In a particularly preferred embodiment, $X^1$ is chlorine or, especially, fluorine and $X^2$ is chlorine or bromine. $W^1$ and $W^2$ are preferably both oxygen.

For compound VII, $R^{15}$ is an alkyl group, preferably of 1 to 4 carbon atoms, which may be substituted or unsubstituted, and:

Z is fluorine, chlorine, bromine, iodine, cyano, nitro, amino, alkoxycarbonylamino of 1 to 6 alkyl carbon atoms, di(alkylcarbonyl)amino in which each alkyl is of 1 to 6 carbon atoms, hydroxysulfonyl, halosulfonyl, alkyl of 1 to 6 carbon atoms, haloalkyl of 1 to 5 carbon atoms, —QR, —CO—$R^6$, —$S(O)_mR^8$, —$Q^2R^9$, —O-$SO_2R^{10}$, NHN=$CR^{11}R^{12}$, or —Q—$CR^3R^4$—CO—$Q^1$—$R^5$;

Q and $Q^1$ are independently O, S, or $NR^7$ in which $R^7$ is hydrogen or alkyl of 1 to 6 carbon atoms;

$Q^2$ is O or S;

R is hydrogen, alkyl of 1 to 6 carbon atoms (which is unsubstituted or substituted with cycloalkyl of 3 to 7 carbon atoms), cycloalkyl of 3 to 7 carbon atoms (which is unsubstituted or substituted with alkyl of 1 to 6 carbon atoms), benzyl, alkoxyalkyl of 2 to 8 carbon atoms, alkoxyalkoxyalkyl of 3 to 8 carbon atoms, alkylthioalkyl, alkylsulfinylalkyl, or alkylsulfonylalkyl of 2 to 8 carbon atoms, tri(alkyl of 1 to 4 carbon atoms)silyl(alkyl of 1 to 4 carbon atoms), cyanoalkyl of 1 to 5 alkyl carbon atoms, alkenyl or haloalkenyl of 2 to 5 carbon atoms, alkynyl or haloalkynyl of 2 to 5 carbon atoms, haloalkyl of 1 to 5 carbon atoms, alkylcarbonyl of 1 to 6 alkyl carbon atoms, or dialkylaminocarbonyl or dialkylaminothiocarbonyl in which each alkyl is of 1 to 6 carbon atoms;

$R^3$ is hydrogen or alkyl of 1 to 4 carbon atoms, and $R^4$ is hydrogen, alkyl of 1 to 4 carbon atoms, or alkoxy of 1 to 4 carbon atoms;

$R^5$ is hydrogen, alkyl of 1 to 6 carbon atoms (which is unsubstituted or substituted with cycloalkyl of 3 to 7 carbon atoms), cycloalkyl of 3 to 7 carbon atoms (which is unsubstituted or substituted with alkyl of 1 to 4 carbon atoms), alkoxyalkyl or alkylthioalkyl of 2 to 6 carbon atoms, haloalkyl or 1 to 5 carbon atoms, alkenyl of 2 to 5 carbon atoms, cycloalkenyl of 5 to 7 carbon atoms (which is unsubstituted or substituted with alkyl of 1 to 4 carbon atoms), cycloalkenylalkyl of 6 to 10 carbon atoms, phenyl or phenylmethyl (each of which is unsubstituted or ring-substituted with fluorine, chlorine, bromine, or alkyl, alkoxy or alkylthio of 1 to 4 carbon atoms), cyanoalkyl of 1 to 5 alkyl carbon atoms, alkynyl of 2 to 5 carbon atoms, alkylimino of 1 to 6 carbon atoms (which is unsubstituted or substituted with cycloalkyl of 3 to 7 carbon atoms), or cycloalkylimino of 5 to 7 carbon atoms (which is unsubstituted or substituted with alkyl of 1 to 4 carbon atoms); or $Q^1$ and $R^5$ together represent a phenylsulfonylamino group in which the phenyl is unsubstituted or substituted with fluorine, chlorine, bromine, alkyl of 1 to 4 carbon atoms, alkoxy of 1 to 4 carbon atoms, or alkoxycarbonyl of 1 to 4 alkyl carbon atoms;

$R^6$ is hydroxy, alkoxy or alkylthio of 1 to 6 carbon atoms, alkoxyalkoxy of 2 to 6 carbon atoms, amino, or alkylamino or dialkylamino wherein each alkyl is of 1 to 6 carbon atoms and is unsubstituted or substituted with alkoxy of 1 to 4 carbon atoms;

$R^8$ is alkyl of 1 to 6 carbon atoms or alkenyl or alkynyl of 2 to 5 carbon atoms and m is 1 or 2;

$R^9$ is a 5- or 6-membered ring heterocyclic group of 1 or 2 same or different heteroatoms selected from O, S, and N or an alkyl radical of 1 to 5 carbon atoms substituted with said heterocyclic group;

$R^{10}$ is alkyl of 1 to 6 carbon atoms (which is unsubstituted or substituted with halogen, cyano, alkoxy or alkylthio of 1 to 4 carbon atoms, or alkylamino or dialkylamino in which alkyl is of 1 to 4 carbon atoms), phenyl, or alkylamino or dialkylamino in which alkyl is of 1 to 4 carbon atoms; and $R^{11}$ is hydrogen or alkyl of 1 to 4 carbon atoms and $R^{12}$ is alkyl of 1 to 4 carbon atoms, or $C(R^{11})(R^{12})$ taken as a unit is cycloalkyl of 3 to 7 carbon atoms.

Preferably Z is fluorine, chlorine, bromine, iodine, cyano, nitro, amino, hydroxysulfonyl, chlorosulfonyl, or a group —OR in which R is alkyl of 1 to 6 carbon atoms, benzyl, alkoxyalkyl of 2 to 4 carbon atoms, or alkenyl or alkynyl of 2 to 5 carbon atoms. In a particularly preferred embodiment Z is —OR in which R is alkyl of 1 to 4 carbon atoms or benzyl.

For compound VIII ($R^1$=H), Z is as defined above for compound VII and $R^2$ is hydrogen, hydroxycarbonyl, or alkyl of 1 to 4 carbon atoms such as methyl. $R^2$ is preferably hydrogen or hydroxycarbonyl.

For compound IX ($R^2$=$CO_2H$), Z is as defined above for compound VII and $R^I$ is alkyl of 1 to 6 carbon atoms, haloalkyl of 1 to 5 carbon atoms, cyanoalkyl of 1 to 5 alkyl carbon atoms, alkenyl or alkynyl of 2 to 5 carbon atoms, alkoxyalkyl, alkylthioalkyl, alkylsulfinylalkyl, or alkylsulfonylalkyl of 2 to 5 carbon atoms. $R^1$ is preferably alkyl of 1 to 4 carbon atoms, cyanoalkyl of 1 to 3 alkyl carbon atoms, fluoroalkyl of 1 to 3 carbon atoms, alkenyl or alkynyl of 3 to 5 carbon atoms, alkoxyalkyl of 2 to 4 carbon atoms, alkylthioalkyl of 2 to 4 carbon atoms, alkylsulfinylalkyl of 2 to 4 carbon atoms, or alkylsulfonylalkyl of 2 to 4 carbon atoms. For example, $R^1$ may be methyl, ethyl, cyanomethyl, 2-propenyl, 2-propynyl, fluoromethyl having 1 or 2 fluorine atoms, 2-fluoroethyl, 3-fluoropropyl, methoxymethyl, methylthiomethyl, methylsulfinylmethyl, or methylsulfonylmethyl, especially methyl.

For compound X (Z=OH, SH, or $NH_2$), $R^1$ is as defined above for compound IX and $R^2$ is hydrogen or alkyl of 1 to 4 carbon atoms such as methyl, $R^2$ is preferably hydrogen.

Representative compounds of the invention are shown in Table 1. Characterizing data for many of the compounds are given in Table 2.

The preparation and herbicidal activity of representative compounds of this invention are illustrated further in the examples below. All temperatures are in degrees Celsius, and all pressures are in mm Hg.

EXAMPLE I 2-(2,4-DICHLOROPHENYL)-4,6-DIMETHYL-1,2,4-TRIAZINE-3,5-(2H,4H)-DIONE

Step A 2-(2,4-Dichlorophenyl)-6-methyl-1,2,4-triazine-3,5(2H,4H)-dione

To a stirred solution of 4.32 g (0.020 mole) of 2,4-dichlorophenylhydrazine hydrochloride in 100 mL of water and 50 mL of ethanol was added dropwise 2.14 g (0.024 mole) of pyruvic acid in 50 mL of water. Upon complete addition, a precipitate formed and was collected by filtration and dried under reduced pressure at ambient temperature. The solid hydrazone product was dissolved in 100 mL of toluene to which 4.8 g (0.041 mole) of thionyl chloride was added. The resultant mixture was stirred and heated at reflux for 0.5 hour. Distillation of the solvent under reduced pressure left a solid residue, which was dissolved in 100 mL of toluene. Urethane (2.2 g, 0.024 mole) was added, and the resultant solution heated at reflux with stirring for two hours. The solvent was removed from the mixture by distillation under reduced pressure to leave a residue. This residue was subjected to column chromatography on silica gel, eluting with ethyl acetate:heptane (1:1). Appropriate fractions were combined, and the solvent removed by evaporation to leave a gummy residue. The residue was dissolved in 75 mL of ethanol and 75 mL of 1N sodium hydroxide. The resultant solution was heated to 60° C., then poured into a mixture of 3N hydrochloric acid and ice. A solid formed which was collected by filtration and dried under reduced pressure. Recrystallization from tetrahydrofuran:heptane provided 2.0 g of 2-(2,4-dichlorophenyl)-6-methyl-1,2,4-triazine-3,5(2H,4H)-dione (mp 197° C. dec), Compound 4 in the tables.

The nmr and ir spectra were consistent with the assigned structure.

Step B 2-(2,4-Dichlorophenyl)-4,6-dimethyl-1,2,4-triazine-3,5(2H,4H)-dione

A solution of 1.1 g (0.0040 mole) of 2-(2,4-dichlorophenyl)-6-methyl-1,2,4-triazine-3,5(2H,4H)-dione in 5 mL of N,N-dimethylformamide was added to a stirred mixture of 0.11 g (0.0045 mole) of sodium hydride in 10 mL of N,N-dimethylformamide. After 0.5 hour, 0.63 g (0.0045 mole) of iodomethane in 5 mL of N,N-dimethylformamide was added, and the resultant mixture was stirred for approximately 18 hours. The mixture was poured into water and the resulting precipitate was collected and dissolved in ethyl acetate. The organic solution was washed with water, dried over anhydrous magnesium sulfate, and filtered. The filtrate was evaporated under reduced pressure to leave a solid. The solid was purified by recrystallization from heptane to yield 0.52 g of 2-(2,4-dichlorophenyl)-4,6-dimethyl-1,2,4-triazine-3,5(2H,4H)-dione (mp 109°-110° C.), Compound 5 in the tables.

The nmr and ir spectra were consistent with the assigned structure.

EXAMPLE II

2-[4-CHLORO-2-FLUORO-5-(1-METHYLETHOXY)PHENYL]-1,2,4-TRIAZINE-3,5(2H,4H)-DIONE

Step A Methyl(2-chloro-4-fluorophenyl)carbonate

To a stirred solution of 20.0 g (0.14 mole) of 2-chloro-4-fluorophenol and 6.64 g (0.17 mole) of sodium hydroxide in 100 mL of water at 15° C. was added 17.7 g (0.19 mole) of methyl chloroformate. After complete addition, the mixture was stirred for 15 minutes then extracted with ethyl acetate. The organic phase was washed with a 1N sodium hydroxide solution, then dried over anhydrous magnesium sulfate. The dried extract was filtered, and the filtrate evaporated under reduced pressure to provide methyl(2-chloro-4-fluorophenyl)carbonate as a solid.

Step B 2-Chloro-4-fluoro-5-nitrophenol

To a stirred mixture of methyl(2-chloro-4-fluorophenol)carbonate prepared in Step A in 21.7 mL of concentrated sulfuric acid was added dropwise 11.1 mL of concentrated nitric acid. The reaction mixture was kept at a temperature below 30° C. throughout the addition. After complete addition, the mixture was stirred at room temperature for one hour, then poured into 500 mL of ice water. The aqueous mixture was extracted with ethyl acetate. The extract was washed in succession with water, saturated aqueous sodium bicarbonate, and saturated aqueous sodium chloride. The washed extract was dried over anhydrous magnesium sulfate, filtered, and the filtrate was evaporated under reduced pressure to leave a solid residue, methyl(2-chloro-4-fluoro-5-nitrophenyl)carbonate. This residue was dissolved in 100 mL of ethanol to which was added 150 mL of a 1N sodium hydroxide solution. The mixture was heated on a steam bath for 30 minutes, cooled, and poured into a mixture of ice and hydrochloric acid. The resultant acidic mixture was extracted with ethyl acetate. The extract was dried over anhydrous magnesium sulfate and was filtered. The filtrate was evaporated under reduced pressure to give an oil which crystallized slowly. Recrystallization from heptane gave 15.8 g of 2-chloro-4-fluoro-5-nitrophenol.

The nmr spectrum was consistent with the assigned structure.

Step C

4-Chloro-2-fluoro-5-(1-methylethoxy)nitrobenzene

To a stirred solution of 15.8 g (0.083 mole) of 2-chloro-4-fluoro-5-nitrophenol in 90 mL of acetone was added 17.1 g (0.12 mole) of potassium carbonate followed by a solution of 21.0 g (0.12 mole) of 2-iodopropane in 10 mL of acetone. After complete addition, the reaction mixture was heated at 60° C. for approximately 18 hours. The mixture was cooled and poured into a mixture of ice and concentrated hydrochloric acid. The resultant mixture was extracted with ethyl acetate, and the extract was washed with a 1N sodium hydroxide solution. The washed extract was dried over anhydrous magnesium sulfate and was filtered. The solvent was evaporated under reduced pressure to leave 17.7 g of 4-chloro-2-fluoro-5-(1-methylethoxy)nitrobenzene as a solid.

Step D 2-[4-Chloro-2-fluoro-5-(1-methylethoxy)phenyl]-1,2,4-triazine-3,5(2H,4H)-dione Hydrogenation of 2.8 g (0.012 mole) of 4-chloro-2-fluoro-5-(1-methylethoxy)nitrobenzene in the presence of 30 mL of acetic acid and 0.2 g of platinum oxide produced 4-chloro-2-fluoro-5-(1-methylethoxy)aniline, which was not isolated from the reaction mixture. The platinum catalyst was removed by filtration, and the filtrate was diluted with 100 mL of water and 10 mL of concentrated hydrochloric acid. The acid solution was cooled to 0° C., and a solution of 0.84 g (0.012 mole) of sodium nitrite in 10 mL of water was added. The solution was stirred at 0° C. for 30 minutes, then a solution of 5.0 g (0.061 mole) of sodium acetate in 10 mL of water was added. After stirring for a short period of time, the solution was added to a mixture of 3.0 g (0.12 mole) of malonyldiurethane [prepared by the method of Backes, et al., *J. Chem. Soc.*, 359, (1921)] and 25.0 g (0.29 mole) of anhydrous sodium acetate in 300 mL of water at 10° C. After complete addition, the mixture was stirred at 10° C. for 30 minutes. The mixture was extracted with ethyl acetate, and the extract washed with a saturated aqueous sodium chloride solution. The washed extract was dried over anhydrous magnesium sulfate, filtered, and the filtrate evaporated under reduced pressure to give 6.0 g of a solid.

The solid was dissolved in a mixture of 80 mL of ethanol and 80 mL of tetrahydrofuran. To this was added 40 mL of a 10% aqueous potassium hydroxide solution. The resultant mixture was stirred for 15 minutes and washed with ethyl acetate. The aqueous phase was made acidic with dilute hydrochloric acid, and the acidic solution extracted with ethyl acetate. The extract was treated with decolorizing charcoal and dried over anhydrous magnesium sulfate. The extract was filtered, and the filtrate was concentrated under reduced pressure to leave 3.2 g of a residue. The residue was heated at 150° C. in 6.0 mL of mercaptoacetic acid for three hours. The mixture was cooled to room temperature, diluted with ethyl acetate, and extracted with a saturated aqueous sodium bicarbonate solution. The organic phase was dried over anhydrous magnesium sulfate and filtered. The solvent was evaporated from the filtrate under reduced pressure to yield 2.0 g of 2-[4-chloro-2-fluoro-5-(1-methylethoxy)phenyl]-1,2,4-triazine-3,5(2H,4H)-dione as an oil, Compound 17 in the tables.

The nmr spectrum was consistent with the assigned structure.

EXAMPLE III

2-[2,4-DICHLORO-5-(2-PROPYNYLOXY)-PHENYL]-4-METHYL-1,2,4-TRIAZINE-3,5(2H,4H)-DIONE

Step A 3-Hydroxyacetanilide

To a stirred solution of 66.0 g (0.60 mole) of 3-aminophenol in 180 mL of water was added dropwise 77.9 g (0.76 mole) of acetic anhydride. After complete addition, the reaction mixture was heated on a steam bath for 10 minutes, then cooled to 0° C. A precipitate formed and was collected by filtration. The filter cake was washed with cold water and dried in a desiccator for two hours to yield 81.0 g of 3-hydroxyacetanilide (mp 144°-146° C.).

Step B 2,4-Dichloro-5-hydroxyacetanilide

Chlorination of 53.0 g (0.35 mole) of 3-hydroxyacetanilide with chlorine gas in 400 mL of glacial acetic acid at 15°-20° C. for one hour produced 23.5 g of 2,4-dichloro-5-hydroxyacetanilide (mp 226°-228° C.).

Step C 2,4-Dichloro-5-(1-methylethoxy)acetanilide

A stirred mixture of 22.0 g (0.1 mole) of 2,4-dichloro-5-hydroxyacetanilide, 25.5 g (0.15 mole) of 2-iodopropane, and 20.7 g (0.15 mole) of potassium carbonate in 150 mL of acetone was heated at reflux temperature for approximately 18 hours. The mixture was cooled, filtered, and the filtrate evaporated under reduced pressure to leave a solid. The solid was recrystallized from ethanol to yield 22.3 g of 2,4-dichloro-5-(1-methylethoxy)acetanilide (mp 129°-130° C.).

Step D 2,4-Dichloro-5-(1-methylethoxy)aniline

A stirred mixture of 22.3 g of 2,4-dichloro-5-(1-methylethoxy) acetanilide, 60 mL of concentrated hydrochloric acid, and 60 mL of water was heated at reflux for 0.5 hour. The mixture was cooled in a refrigerator, and the resulting precipitate was collected by filtration. The solid was suspended in water, and the mixture was treated with sodium carbonate until it was slightly basic. The resultant mixture was extracted with diethyl ether. The extract was washed with water, and the ether removed by distillation under reduced pressure to leave an oil. Distillation of the oil under reduced pressure produced 14.0 g of 2,4-dichloro-5-(1-methylethoxy)aniline (bp 102° C. at 0.1 mm Hg).

Step E 2-[2,4-Dichloro-5-(1-methylethoxy)-phenyl]-1,2,4-triazine-3,5(2H,4H)-dione-6-carboxylic acid To a stirred mixture of 10.0 g (0.045 mole) of 2,4-dichloro-5-(1-methylethoxy)aniline in 200 mL of water was added 30 mL of concentrated hydrochloric acid. The resultant mixture was cooled to 0° C., and a solution of 3.13 g (0.45 mole) of sodium nitrite in 30 mL of water was added during 15 minutes. After complete addition, 30.0 g (0.35 mole) sodium acetate in 60 mL of water was added, and the resulting mixture was stirred at 0° C. for one hour. The cold reaction mixture was added portionwise to a stirred solution of 11.7 g (0.0477 mole) of malonyldiurethane [prepared by the method of Backes, et al., *J. Chem. Soc.*, 350, (1921)] and 50.0 g (0.59 mole) of anhydrous sodium acetate in 1500 mL of water at 0° C. After complete addition the mixture was stirred at 0° C. for one hour, and the resulting precipitate was collected by filtration and washed with water. The filter cake was dissolved in a mixture of 250 mL of tetrahydrofuran and 250 mL of ethanol. To this solution was added 150 mL of a 10% aqueous potassium hydroxide solution. The resultant mixture was stirred for 0.5 hour and made acidic with 60 mL of concentrated hydrochloric acid. Most of the tetrahydrofuran was removed from the mixture by evaporation under reduced pressure to leave an aqueous residue. The residue was extracted with ethyl acetate, and the extract treated with decolorizing charcoal. The extract was dried over anhydrous magnesium sulfate and filtered. The filtrate was evaporated under reduced pressure to leave 17.9 g of 1-[2,4-dichloro-5-(1-methylethoxy)phenyl]-1,2,4-triazine-3,5(2H,4H)-dione-6-carboxylic acid, Compound 11 in the tables.

The preparation of Compound 11 was repeated. The product was found to have a melting point of 195°-197° C. (dec.) and its nmr and ir spectra were consistent with the assigned structure.

Step F

2-[2,4-Dichloro-5-(1-methylethoxy)phenyl]-1,2,4-triazine-3,5(2H,4H)-dione

A stirred mixture of 10.0 g (0.028 mole) of 2-[2,4-dichloro-5-(1-methylethoxy)phenyl]-1,2,4-triazine-3,5-(2H,4H)-dione-6-carboxylic acid in 10 mL of mercaptoacetic acid was heated at 140° C. for two hours. The reaction mixture was cooled to room temperature and partitioned between ethyl acetate and saturated aqueous sodium bicarbonate. The organic phase was washed with two portions of saturated aqueous sodium bicarbonate, and then with saturated aqueous sodium chloride. The washed organic phase was dried over anhydrous magnesium sulfate and filtered. The filtrate was evaporated under reduced pressure to yield 7.5 g of 2-[2,4-dichloro-5-(1-methylethoxy)phenyl]-1,2,4-triazine-3,5(2H,4H)-dione, Compound 51 in the tables.

Compound 6 in the tables was prepared in a similar manner (Step E and F) from the appropriately substituted aniline.

Step G

2-[2,4-Dichloro-5-(1-methylethoxy)phenyl]-4-methyl-1,2,4-triazine-3,5(2H,4H)-dione To a stirred mixture of 0.6 g (0.025 mole) of sodium hydride in 15 mL of N,N-dimethylformamide was added a solution of 7.5 g (0.024 mole) of 2-[2,4-dichloro-5-(1-methylethoxy)phenyl]-1,2,4-triazine-3,5(2H,4H)-dione in 30 mL of N,N-dimethylformamide with external cooling to maintain the reaction temperature below 40° C. After complete addition, the mixture was allowed to come to room temperature and was stirred for one hour. A solution of 3.5 g (0.025 mole) of iodomethane in 10 mL of N,N-dimethylformamide was added to the reaction mixture, and stirring was continued for an additional hour at room temperature. The reaction mixture was poured into ice water, and the mixture was extracted with ethyl acetate. The extract was dried over anhydrous magnesium sulfate and filtered. The filtrate was evaporated under reduced pressure to produce 2-[2,4-dichloro-5-(1-methylethoxy)phenyl]-4-methyl-1,2,4-triazine-3,5(2H,4H)-dione as an oil, Compound 12 in the tables.

The preparation of Compound 12 was repeated. The product was found to have a melting point of 111°-112° C. after chromatographic purification on a silica gel column. The nmr and ir spectra of this sample were consistent with the assigned structure. Compounds 2, 7, 8, and 18 were also prepared in this manner from the appropriately substituted anilines (prepared by the methods of Example III, Steps E and F) and iodomethane. Compounds 3, 15 and 19 were prepared from 3-bromo-1-propene and the appropriately substituted triazinedione. Similarly, reaction of the appropriately substituted triazinedione with propargyl bromide, bromoethane, and 1-chloro-2-fluoroethane gave Compounds 25, 29, and 41 respectively.

Step H 2-(2,4-Dichloro-5-hydroxyphenyl)-4-methyl-1,2,4-triazine-3,5(2H,4H)-dione The oil prepared in Step G (Compound 12) was stirred with 10 mL of concentrated sulfuric acid at 0° C. for 10 minutes, and the mixture was poured into ice water. The aqueous mixture was extracted with ethyl acetate, and the solvent was removed from the extract by evaporation under reduced pressure to give a residue. The residue was purified by column chromatography on silica gel, eluting with ethyl acetate:heptane (1:1). Evaporation of the appropriate fractions gave 4.4 g of 2-(2,4-dichloro-5-hydroxyphenyl)-4-methyl-1,2,4-triazine-3,5-(2H,4H)-dione (mp 199°-201° C.), Compound 9 in the tables.

The nmr spectrum was consistent with the assigned structure.

Step I

2-[2,4-Dichloro-5-(2-propynyloxy)phenyl]-4-methyl-1,2,4-triazine-3,5(2H,4H)-dione Under a dry nitrogen atmosphere a solution of 1.0 g (0.003 mole) of 2-(2,4-dichloro-5-hydroxyphenyl)-4-methyl-1,2,4-triazine-3,5(2H,4H)-dione in 15 mL of N,N-dimethylformamide was added slowly to a stirred mixture of 0.09 g (0.0037 mole) of sodium hydride in 15 mL of N,N-dimethylformamide. After complete addition, the mixture was stirred at 28° C. until hydrogen evolution ceased, then at 45° C. for 30 minutes. The reaction mixture was cooled to room temperature, and a solution of 0.57 g (0.0038 mole) of 3-bromo-1-propyne in 5 mL of N,N-dimethylformamide was added. The mixture was stirred at room temperature for approximately 18 hours, poured into water, and extracted with ethyl acetate. The extract was washed with a saturated aqueous sodium chloride solution, dried over anhydrous magnesium sulfate, and filtered. The solvent was removed from the filtrate by evaporation under reduced pressure to leave an oil. The oil was purified by preparative chromatography on silica gel, eluting with ethyl acetate:heptane (1:1), to yield 0.8 g of 2-[2,4-dichloro-5-(2-propynyloxy)phenyl]-4-methyl-1,2,4-triazine-3,5(2H,4H)-dione (mp 119°-120° C.), Compound 20 in the tables.

The nmr and ir spectra were consistent with the assigned structure.

Compound 21, 2-[4-chloro-2-fluoro-5-(2-propynyloxy)phenyl]-4-methyl-1,2,4-triazine-3,5(2H,4H)-dione, was also prepared by the method of Example III, Steps H and I, from the appropriately substituted triazinedione.

EXAMPLE IV

2-[2,4-DICHLORO-5-(1-METHYLETHOXY)-PHENYL]-4,6-DIMETHYL-1,2,4-TRIAZINE-3,5(2H,4H)-DIONE

Step A 2,4-Dichloro-5-(1-methylethoxy)phenylhydrazine

A solution of 15.8 g (0.23 mole) of sodium nitrite in 100 mL of water was added to a stirred solution of 50.0 g (0.23 mole) of 2,4-dichloro-5-(1-methylethoxy)aniline in 250 mL of concentrated hydrochloric acid at 0° C. over 30 minutes. After complete addition, the mixture was stirred at 0° C. for 30 minutes. A solution of 114.0 g (0.506 mole) of tin (II) chloride dihydrate in 125 mL of concentrated hydrochloric acid was added dropwise to the reaction mixture. After complete addition, the mixture was stirred for one hour. The resultant white slurry was filtered. The filter cake was added to a 20% aqueous sodium hydroxide solution and stirred for 30 minutes. The basic mixture was filtered, and the filter cake recrystallized from methanol and water to yield 37.0 g of 2,4-dichloro-5-(1-methylethoxy)phenylhydrazine.

Step B

1-[2,4-Dichloro-5-(1-methylethoxy)phenyl]-3,3-dimethyl-1,2,4-triazolidin-5-one

To a stirred solution of 12.7 g (0.054 mole) of 2,4-dichloro-5-(1-methylethoxy)phenylhydrazine in a mixture of 100 mL of tetrahydrofuran and 30 mL of acetone was added 0.5 mL of a 2N sulfuric acid solution. The reaction mixture was stirred at room temperature for 30 minutes after which the solvent was removed by evaporation under reduced pressure. The residue was dissolved in ethyl acetate, and the organic solution was washed with water. The washed organic solution was dried over anhydrous magnesium sulfate, filtered, and the filtrate evaporated under reduced pressure leaving 14.6 g of an oil. The oil was dissolved in 50 mL of glacial acetic acid and 2 mL of water. To this solution was added portionwise 4.5 g (0.56 mole) of potassium cyanate. After complete addition, the mixture was stirred at room temperature for approximately 18 hours. An additional 0.5 g of potassium cyanate was added, and the reaction mixture was stirred for five hours. The mixture was then diluted with water and extracted with ethyl acetate. The extract was dried over anhydrous magnesium sulfate, filtered, and the filtrate evaporated under reduced pressure leaving an oil. The oil was dissolved in 20 mL of ethyl acetate and, upon the addition of 10 mL of heptane, formed a precipitate. The precipitate was collected by filtration and recrystallized from ethyl acetate and heptane to give 4.5 g of 1-[2,4-dichloro-5-(1-methylethoxy)phenyl]-3,3-dimethyl-1,2,4-triazolidin-5-one (mp 162°-163° C.).

The nmr and ir spectra were consistent with the assigned structure.

Step C

2-[2,4-Dichloro-5-(1-methylethoxy)phenyl]-6-methyl-1,2,4-triazine-3,5(2H,4H)-dione To a stirred mixture of 1.0 g (0.0031 mole) of 1-[2,4-dichloro-5-(1-methylethoxy)phenyl]-3,3-dimethyl-1,2,4-triazolidin-5-one in 10 mL of p-dioxane was added 0.29 g (0.0031 mole) of pyruvic acid and one drop of concentrated sulfuric acid. The mixture was stirred at room temperature for one hour, then an additional 0.25 g (0.0029 mole) of pyruvic acid was added. The mixture was heated at 90° C. for three hours, then poured into water. The mixture was extracted with ethyl acetate, and the solvent was evaporated from the extract under reduced pressure to give an oil. The oil was purified by thin-layer preparative chromatography on silica gel, eluting with ethyl acetate:heptane (1:1). Extraction of the appropriate bands gave 0.6 g of 2-[2,4-dichloro-5-(1-methylethoxy)phenyl]-6-methyl-1,2,4-triazine-3,5(2H,4H)-dione as a solid (mp 163°-164° C.), Compound 10 in the tables.

The nmr and ir spectra were consistent with the assigned structure.

Step D

2-[2,4-Dichloro-5-(1-methylethoxy)phenyl]-4,6-dimethyl-1,2,4-triazine-3,5(2H,4H)-dione In a manner similar to Example III, Step G, the reaction of 0.28 g (0.00085 mole) of 2-[2,4-dichloro-5-(1-methylethoxy)phenyl]-6-methyl-1,2,4-triazine-3,5(2H,4H)-dione with 0.037 g (0.00093 mole) of sodium hydride (60% in oil) and 0.13 g (0.00093 mole) of iodomethane in 10 mL of N,N-dimethylformamide produced 0.19 g of 2-[2,4-dichloro-5-(1-methylethoxy)phenyl]-4,6-dimethyl-1,2,4-traizine-3,5(2H,4H)-dione as a low melting solid, Compound 13 in the tables.

The nmr and ir spectra were consistent with the assigned structure.

Compound 16, 2-[2,4-dichloro-5-(1-methylethoxy)phenyl]-6-methyl-4-(2-propenyl)-1,2,4-triazine-3,5(2H,4H)-dione, was also prepared by the method of Example IV using 3-bromo-1-propene rather than iodomethane in Step D. Similarly, Compound 50, 2-[4-chloro-2-fluoro-5-(1-methylethoxy)phenyl]-4-(3-fluoropropyl)-1,2,4-triazine-3,5(2H,4H)-dione, was prepared by treating Compound 17 (Example II D) with 1-chloro-3-fluoropropane.

EXAMPLE V

2-[2,4-DICHLORO-5-(1-METHYLETHOXY)-PHENYL]-4-METHYL-1,2,4-TRIAZINE-3,5(2H,4H)-DIONE-6-CARBOXYLIC ACID

In a manner similar to Example III, Step G, the reaction of 6.6 g (0.018 mole) of 2-[2,4-dichloro-5-(1-methylethoxy)phenyl]-1,2,4-triazine-3,5(2H,4H)-dione-6-carboxylic acid (Compound 11, Example III E) with 1.5 g (0.037 mole) of sodium hydride (60% in oil) and 2.6 g (0.018 mole) of iodomethane in 35 mL of N,N-dimethylformamide produced 2.1 g of 2-[2,4-dichloro-5-(1-methyethoxy)phenyl]-4-methyl-1,2,4-triazine-3,5-(2H,4H)-dione-6-carboxylic acid as a solid (mp 230° C. d), Compound 14 in the tables.

The nmr and ir spectra were consistent with the assigned structure.

EXAMPLE VI

ETHYL 2,4-DICHLORO-5-[4-METHYL-1,2,4-TRIAZINE-3,5(2H,4H)-DIONE-2-YL]-PHENOXYACETATE

In a manner similar to Example II, Step C, the reaction of 0.86 g (0.0030 mole) of 2-(2,4-dichloro-5-hydroxyphenyl)-4-methyl-1,2,4-triazine-3,5(2H,4H)-dione (Compound 9, Example III H) with 0.62 g (0.0045 mole) of potassium carbonate and 0.75 g (0.0045 mole) of ethyl bromoacetate in 10 mL of acetone produced an oil. The oil crystallized upon treatment with heptane to yield 0.85 g of ethyl 2,4-dichloro-5-[4-methyl-1,2,4-triazine-3,5(2H,4H)-dione-2-yl]phenoxyacetate (mp 115°-117° C.), Compound 22 in the tables.

The nmr and ir spectra were consistent with the assigned structure.

Compounds 27 and 28 were prepared in a similar manner by treatment of Compound 9 with ethyl 2-bromopropionate and chloroacetonitrile respectively. The nmr and ir spectra were consistent with the assigned structures.

EXAMPLE VII 2-(2,4-DICHLORO-5-METHYLSULFONYLOXY-PHENYL)-4-METHYL-1,2,4-TRIAZINE-3,5(2H,4H)-DIONE

A solution of 0.35 g (0.0031 mole) of methanesulfonyl chloride in 5 mL of tetrahydrofuran was added to a stirred solution of 0.8 g (0.0028 mole) of 2-(2,4-dichloro-5-hydroxyphenyl)-4-methyl-1,2,4-triazine-3,5-(2H,4H)-dione (Compound 9, Example III H) and 0.30 g (0.0031 mole) of triethylamine in 10 mL of tetrahydrofuran. The reaction mixture was stirred at room temperature for approximately 18 hours, then diluted with water. The resultant mixture was extracted with ethyl acetate, and the extract was dried over anhydrous magnesium sulfate. The dried extract was filtered, and the filtrate was evaporated under reduced pressure to give 0.81 g of 2-(2,4-dichloro-5-methylsulfonyloxyphenyl)-4-methyl-1,2,4-triazine-3,5(2H,4H)-dione as a solid, Compound 23 in the tables.

The nmr and ir spectra were consistent with the assigned structure.

EXAMPLE VIII

2-[2,4-DICHLORO-5-(1-METHYLETHOXY)-PHENYL]-4-(2-FLUOROETHYL)-1,2,4-TRIAZINE-3,5(2H,4H)-DIONE

To a stirred mixture of 0.084 g (0.0035 mole) of sodium hydride in 20 mL of tetrahydrofuran was added a solution of 1.0 g (0.003 mole) of 2-[2,4-dichloro-5-(1-methylethoxy)phenyl]-1,2,4-triazine-3,5(2H,4H)-dione (Compound 51, Example III, Step F) in 5 mL of tetrahydrofuran. The resulting mixture was stirred at room temperature for one hour. Tetrabutylammonium bromide (0.5 g, 0.002 mole) and potassium hydroxide (0.5 g, 0.009 mole) were added, and the mixture was heated at 60°-70° C. for approximately 1.5 hours. While maintaining the temperature at 60° C., a solution of 0.5 g (0.004 mole) of 1-bromo-2-fluoroethane in 5 mL of tetrahydrofuran was added. After complete addition, the mixture was allowed to cool to room temperature and was stirred for approximately 18 hours. The mixture was partitioned between dilute aqueous hydrochloric acid and ethyl acetate. The organic phase was dried over anhydrous magnesium sulfate and filtered. Evaporation of the filtrate under reduced pressure produced an oil. The oil was subjected to column chromatography on silica gel, eluting with ethyl acetate:n-heptane (1:1). Evaporation of the appropriate fractions provided a solid which was recrystallized from ethyl acetate:n-heptane to give 0.4 g of 2-[2,4-dichloro-5-(1-methylethoxy)-phenyl]-4-(2-fluoroethyl)-1,2,4-triazine-3,5(2H,4H)-dione, Compound 26 in the tables.

The nmr spectrum was consistent with the assigned structure.

EXAMPLE IX

2-[4-CHLORO-2-FLUORO-5-(3-BROMO-2-PROPYNYLOXY)PHENYL]-4-METHYL-1,2,4-TRIAZINE-3,5(2H,4H)-DIONE

To a stirred mixture of 0.05 g (0.002 mole) of sodium hydride in 5 mL of tetrahydrofuran was added a solution of 0.55 g (0.0018 mole) of 2-[4-chloro-2-fluoro-5-(2-propynyloxy)phenyl]-4-methyl-1,2,4-triazine-3,5(2H,4H)-dione (Compound 21, see Example III, Step J) in 5 mL of tetrahydrofuran. To this mixture was added a solution of 0.28 g (0.0018 mole) of bromine in 5 mL of tetrahydrofuran. After complete addition, the reaction mixture was stirred at room temperature for one hour. Water, 5 mL, was added to the mixture, and the total stirred at room temperature for two days. The mixture was partitioned between water and ethyl acetate. The organic phase was dried over anhydrous magnesium sulfate and filtered. The filtrate was evaporated under reduced pressure to yield 0.45 g of 2-[4-chloro-2-fluoro-5-(3-bromo-2-propynyloxy)phenyl]-4-methyl-1,2,4-triazine-3,5(2H,4H)-dione as a solid (mp 127°-129° C.), Compound 48 in the tables.

The nmr spectrum was consistent with the assigned structure.

EXAMPLE X

METHYL 2-[2-CHLORO-4-FLUORO-5-(2,3,4,5-TETRAHYDRO-4-METHYL-3,5-DIOXO-1,2,4-TRIAZIN-2-YL)PHENOXY]-PROPIONATE

Step A

2-(4-Chloro-2-fluoro-5-hydroxyphenyl)-4-methyl-1,2,4-triazine-3,5(2H,4H)-dione Treatment of 2-[4-chloro-2-fluoro-5-(1-methylethoxy)phenyl]-4-methyl-1,2,4-triazine-3,5(2H,4H)-dione (Compound 18, see Example III G) with sulfuric acid in the manner of Example III H produced the phenolic compound 2-(4-chloro-2-fluoro-5-hydroxyphenyl)-4-methyl-1,2,4-triazine-3,5-(2H,4H)-dione, Compound 30 in the tables.

The nrm spectrum was consistent with the assigned structure.

Step B Methyl 2-[2-chloro-4-fluoro-5-(2,3,4,5-tetrahydro-4-methyl-3,5-dioxo-1,2,4-triazin-2-yl)phenoxy]proprionate Treatment of Compound 30 with methyl 2-chloropropionate in the presence of potassium carbonate in the manner of Example VI gave methyl 2-[2-chloro-4-fluoro-5-(2,3,4,5-tetrahydro-4-methyl-3,5-dioxo-1,2,4-triazin-2-yl)phenoxy]propionate, Compound 42 in the tables.

The nmr spectrum was consistent with the assigned structure.

Compounds 43, 44 and 49 were prepared in a similar manner by treatment of 2-(4-chloro-2-fluoro-5-hydroxyphenyl)-4-methyl-1,2,4-triazine-3,5(2H,4H)-dione with ethyl chloroacetate, propargyl bromide, and iodoacetamide respectively.

The nmr and ir spectra were consistent with the assigned structures.

Other compounds of the invention may be prepared by the methods exemplified above or by methods within the skill of the art.

HERBICIDAL ACTIVITY

The plant test species used in demonstrating the herbicidal activity of compounds of this invention include cotton (*Gossypium hirsutum* var. Stoneville), soybean (*Glycine max* var. Williams), field corn (*Zea mays* var. Agway 595S), wheat (*Triticum aestivium* var. Prodax), field bindweed (*Convolvulus arvensis*), morningglory (*Ipomea lacunosa* or *Ipomea hederacea*), velvetleaf (*Abutilon theophrasti*), barnyardgrass (*Echinochloa crus galli*), green foxtail (*Setaria viridis*), and johnsongrass (*Sorghum halepense*).

Seeds or tubers of the plant test species were planted in furrows in steam sterilized sandy loam soil contained in disposable fiber flats. A topping soil of equal portions of sand and sandy loam soil was placed uniformly on top of each flat to a depth of approximately 0.5 cm.

The flats for the preemergence test were watered, then drenched with the appropriate amount of a solution of the test compound in a mixture of acetone and water containing a small amount (up to 0.5% v/v) of sorbitan monolaurate emulsifier/solubilizer. The concentration of the test compound in solution was varied to give a range of application rates, generally 8.0 kg/ha and submultiples thereof. The flats were placed in a greenhouse and watered regularly at the soil surface for 21 days at which time phytotoxicity data were recorded.

The flats for the postemergence test were placed in a greenhouse and watered for 8-10 days, then the foliage of the emerged test plants was sprayed with a solution of the test compound in acetone-water containing up to 0.5% sorbitan monolaurate. After spraying the foliage was kept dry for 24 hours, then watered regularly for 21 days, and phytotoxicity data recorded.

Phytotoxicity data were taken either as percent kill or percent control. Percent control was determined by a method similar to the 0 to 100 rating system disclosed in "Research Methods In Weed Science," 2nd ed., B. Truelove, Ed.; Southern Weed Science Society; Auburn University, Auburn, Ala., 1977. The present rating system is as follows:

Herbicide Rating System

| Rating Percent Control | Description of Main Categories | Crop Description | Weed Description |
|---|---|---|---|
| 0 | No effect | No crop reduction or injury | No weed control |
| 10 | | Slight discoloration or stunting | Very poor weed control |
| 20 | Slight effect | Some discoloration, stunting or stand loss | Poor weed control |
| 30 | | Crop injury more pronounced but not lasting | Poor to deficient weed control |
| 40 | | Moderate injury, crop usually recovers | Deficient weed control |
| 50 | Moderate effect | Crop injury more lasting, recovery | Deficient to moderate weed control |
| 60 | | Lasting crop injury no recovery | Moderate weed control |
| 70 | | Heavy injury and stand loss | Control somewhat less than satisfactory |
| 80 | Severe effect | Crop nearly destroyed a few survivors | Satisfactory to good weed control |
| 90 | | Only occasional live plants left | Very good to excellent control |
| 100 | Complete effect | Complete crop destruction | Complete weed destruction |

Herbicidal data at selected application rates are given for various compounds of the invention in Table 3 and Table 4 below. The test compounds are identified therein by numbers which correspond to those in Table 1.

In Tables 3 and 4 below:

"kg/ha" is kilograms per hectare,

"% K" is percent kill, and

"%C" is percent control.

It is clear from the data that the generic class of aryltriazinediones and sulfur analogs thereof described and illustrated herein is characterized by herbicidal activity, and that the degree of this activity varies among specific compounds within this class and to some extent among the species of plant to which these compounds may be applied. Thus, selection of a specific herbicidal compound for control of a specific plant may readily be made.

For herbicidal application, the active compounds as above defined are formulated into herbicidal compositions, by admixture, in herbicidally effective amounts, with adjuvants and carriers normally employed in the art for facilitating the dispersion of active ingredients for the particular utility desired, recognizing the fact that the formulation and mode of application of a toxicant may affect the activity of the material in a given application. Thus, for agricultural use the present herbicidal compounds may be formulated as granules of relatively large particle size, as water-soluble or water-dispersible granules, as powdery dusts, as wettable powders, as emulsifiable concentrates, as solutions, or as any of several other known types of formulations, depending on the desired mode of application.

For preemergence application these herbicidal compositions are usually applied either as sprays, dusts, or granules in the areas in which suppression of vegetation is desired. For postemergence control of established plant growth, sprays or dusts are most commonly used. These formulations may contain as little as 0.5% to as much as 95% or more by weight of active ingredient.

Dusts are free flowing admixtures of the active ingredient with finely divided solids such as talc, natural clays, kieselguhr, flours such as walnut shell and cottonseed flours, and other organic and inorganic solids which act as dispersants and carriers for the toxicant; these finely divided solids have an average particle size of less than about 50 microns. A typical dust formulation useful herein is one containing 1.0 part of the herbicidal compound and 99.0 parts of talc.

Wettable powders, also useful formulations for both pre- and postemergence herbicides, are in the form of finely divided particles which disperse readily in water or other dispersant. The wettable powder is ultimately applied to the soil either as a dry dust or as an emulsion in water or other liquid. Typical carriers for wettable powders include Fuller's earth, kaolin clays, silicas, and other highly absorbent, readily wet inorganic diluents. Wettable powders normally are prepared to contain about 5-80% of active ingredient, depending on the absorbency of the carrier, and usually also contain a small amount of a wetting, dispersing or emulsifying agent to facilitate dispersion. For example, a useful wettable powder formulation contains 80.8 parts of the herbicidal compound, 17.9 parts of Palmetto clay, and 1.0 part of sodium lignosulfonate and 0.3 part of sulfonated aliphatic polyester as wetting agents. Frequently, additional wetting agent and/or oil will be added to the tank-mix for postemergence application to facilitate dispersion on the foliage and absorption by the plant.

Other useful formulations for herbicidal applications are emulsifiable concentrates. Emulsifiable concentrates are homogeneous liquid or paste compositions dispersible in water or other dispersant, and may consist entirely of the herbicidal compound and a liquid or solid emulsifying agent, or may also contain a liquid carrier, such as xylene, heavy aromatic naphthas, isophorone, or other non-volatile organic solvent. For herbicidal application these concentrates are dispersed in water or other liquid carrier, and normally applied as a spray to the area to be treated. The percentage by weight of the essential active ingredient may vary according to the manner in which the composition is to be applied, but in general comprises 0.5 to 95% of active ingredient by weight of the herbicidal composition.

Typical wetting, dispersing, or emulsifying agents used in agricultural formulations include, for example, the alkyl and alkylaryl sulfonates and sulfates and their sodium salts, polyhydric alcohols, and other types of surface active agents, many of which are available in commerce. The surface active agent, when used, normally comprises 1% to 15% by weight of the herbicidal composition.

Other useful formulations for herbicidal applications include simple solutions of the active ingredient in a solvent in which it is completely soluble at the desired concentration, such as acetone, alkylated naphthalenes, xylene, or other organic solvents. Granular formulations, wherein the toxicant is carried on relatively coarse particles, are of particular utility for aerial distribution or for penetration of cover crop canopy. Pressurized sprays, typically aerosols wherein the active ingredient is dispersed in finely divided form as a result of vaporization of a low boiling dispersant solvent carrier, such as the Freons, may also be used. Water-soluble or water-dispersible granules are also useful formulations for herbicidal application of the present compounds. Such granular formulations are free-flowing, non-dusty, and readily water-soluble or water-miscible. The soluble or dispersible granular formulations described in U.S. Pat. No. 3,920,442 are useful herein with the present herbicidal compounds.

The active herbicidal compounds of this invention may be formulated and/or applied with insecticides, fungicides, nematicides, plant growth regulators, fertilizers, or other agricultural chemicals and may be used as effective soil sterilants as well as selective herbicides in agriculture. In applying an active compound of this invention, whether formulated alone or with other agricultural chemicals, an effective amount and concentration of the active compound is of course employed.

The active herbicidal compounds of this invention may be used in combination with other herbicides, e.g. they may be mixed with, say, an equal or larger amount of a known herbicide such as chloroacetanilide herbicides such as 2-chloro-N-(2,6-diethylphenyl)-N-(methoxymethyl)acetamide (alachlor), 2-chloro-N(2-ethyl-6-methylphenyl)-N-(2-methoxy-1-methylethyl)acetamide (metolachlor), and N-chloroacetyl-N-(2,6-diethylphenyl)glycine (diethatyl-ethyl); benzothiadiazinone herbicides such as 3-(1-methylethyl)-(1H)-2,1,3-benzothiadiazin-4-(3H)-one-2,2-dioxide (bentazon); triazine herbicides such as 6-chloro-N-ethyl-N-(1-methylethyl)-1,3,5-triazine-2,4-diamine (atrazine), and 2-[4-chloro-6-(ethylamino)-1,3,5-triazin-2-yl]amino-2-methylpropanenitrile (cyanazine); dinitrolaniline herbicides such as 2,6-dinitro-N,N-dipropyl-4-(trifluoromethyl)-benzeneamine (trifluralin); and aryl urea herbicides such as N'-(3,4-dichlorophenyl)-N,N-dimethylurea (diuron) and N,N-dimethyl-N'-[3-(trifluoromethyl)phenyl]urea (fluometuron).

It is apparent that various modifications may be made in the formulation and application of the compounds of this invention without departing from the inventive concepts herein as defined in the claims.

TABLE 1

Representative Compounds

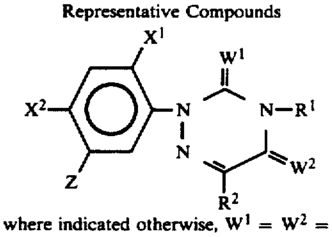

(Except where indicated otherwise, $W^1 = W^2 =$ oxygen).

| Compound Number | $X^1$ | $X^2$ | Z | $R^1$ | $R^2$ |
|---|---|---|---|---|---|
| 1 | H | H | H | $CH_3$ | H |
| 2 | F | H | H | $CH_3$ | H |
| 3 | H | Cl | H | $CH_2CH{=}CH_2$ | H |
| 4 | Cl | Cl | H | H | $CH_3$ |
| 5 | Cl | Cl | H | $CH_3$ | $CH_3$ |
| 6 | F | Cl | H | H | H |
| 7 | F | Cl | H | $CH_3$ | H |
| 8[4] | Cl | Cl | H | $CH_3$ | H |
| 9 | Cl | Cl | OH | $CH_3$ | H |
| 10 | Cl | Cl | $OCH(CH_3)_2$ | H | $CH_3$ |
| 11 | Cl | Cl | $OCH(CH_3)_2$ | H | $CO_2H$ |
| 12 | Cl | Cl | $OCH(CH_3)_2$ | $CH_3$ | H |
| 13 | Cl | Cl | $OCH(CH_3)_2$ | $CH_3$ | $CH_3$ |
| 14 | Cl | Cl | $OCH(CH_3)_2$ | $CH_3$ | $CO_2H$ |
| 15 | Cl | Cl | $OCH(CH_3)_2$ | $CH_2CH{=}CH_2$ | H |
| 16 | Cl | Cl | $OCH(CH_3)_2$ | $CH_2CH{=}CH_2$ | $CH_3$ |
| 17 | F | Cl | $OCH(CH_3)_2$ | H | H |
| 18 | F | Cl | $OCH(CH_3)_2$ | $CH_3$ | H |
| 19 | F | Cl | $OCH(CH_3)_2$ | $CH_2CH{=}CH_2$ | H |
| 20 | Cl | Cl | $OCH_2C{\equiv}CH$ | $CH_3$ | H |
| 21 | F | Cl | $OCH_2C{\equiv}CH$ | $CH_3$ | H |
| 22 | Cl | Cl | $OCH_2CO_2C_2H_5$ | $CH_3$ | H |
| 23 | Cl | Cl | $OSO_2CH_3$ | $CH_3$ | H |
| 24[1] | F | Cl | $OCH_2C{\equiv}CH$ | $CH_3$ | H |
| 25 | Cl | Cl | $OCH(CH_3)_2$ | $CH_2C{\equiv}CH$ | H |
| 26 | Cl | Cl | $OCH(CH_3)_2$ | $CH_2CH_2F$ | H |
| 27 | Cl | Cl | $OCH(CH_3)CO_2C_2H_5$ | $CH_3$ | H |
| 28 | Cl | Cl | $OCH_2CN$ | $CH_3$ | H |
| 29 | Cl | Cl | $OCH(CH_3)_2$ | $C_2H_5$ | H |
| 30 | F | Cl | OH | $CH_3$ | H |
| 31 | H | Cl | H | H | $CO_2H$ |
| 32 | H | Cl | $OCH_3$ | H | $CO_2H$ |
| 33 | H | Cl | H | H | H |
| 34 | H | $CH_3$ | H | H | H |

TABLE 1-continued

Representative Compounds

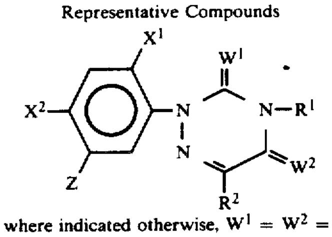

(Except where indicated otherwise, $W^1 = W^2 =$ oxygen).

| Compound Number | $X^1$ | $X^2$ | Z | $R^1$ | $R^2$ |
|---|---|---|---|---|---|
| 35 | H | $CH_3$ | H | $CH_3$ | H |
| 36 | H | Cl | H | $CH_3$ | H |
| 37 | H | Cl | $OCH_3$ | H | H |
| 38 | H | $OCH_3$ | H | H | H |
| 39 | H | Cl | $OCH_3$ | $CH_3$ | H |
| 40 | H | $OCH_3$ | H | $CH_3$ | H |
| 41 | F | Cl | $OCH(CH_3)_2$ | $CH_2F$ | H |
| 42 | F | Cl | $OCH(CH_3)CO_2CH_2$ | $CH_3$ | H |
| 43 | F | Cl | $OCH_2CO_2C_2H_5$ | $CH_3$ | H |
| 44 | F | Cl | $OCH_2C\equiv CH$ | $CH_2F$ | H |
| 45 | F | Cl | $OCH(CH_3)_2$ | $CH_2CN$ | H |
| 46 | F | Cl | $NO_2$ | $CH_3$ | H |
| 47 | F | Cl | $NH_2$ | $CH_3$ | H |
| 48 | F | Cl | $OCH_2C\equiv CBr$ | $CH_3$ | H |
| 49 | F | Cl | $OCH_2CONH_2$ | $CH_3$ | H |
| 50 | F | Cl | $OCH(CH_3)_2$ | $CH_2(CH_2)_2F$ | H |
| 51 | Cl | Cl | $OCH(CH_3)_2$ | H | H |
| 52 | F | Cl | $OCH_2C\equiv CI$ | $CH_3$ | H |
| 53 | F | Br | $OCH(CH_3)_2$ | $CH_3$ | H |
| 54 | F | H | $OCH(CH_3)_2$ | $CH_3$ | H |
| 55 | F | $CH_3$ | $OCH(CH_3)_2$ | $CH_3$ | H |
| 56 | F | $CF_3$ | $OCH_2C\equiv CH$ | $CH_3$ | H |
| 57 | F | $OC_6H_5$ | $OCH_2C\equiv CH$ | $CH_3$ | H |
| 58 | F | $OCH_2C_6H_5$ | $OCH(CH_3)_2$ | $CH_3$ | H |
| 59 | F | Cl | $NHCH_3$ | $CH_3$ | H |
| 60 | F | Cl | $N(CH_3)_2$ | $CH_3$ | H |
| 61[1] | F | Cl | $OSO_2CH_3$ | $CH_3$ | H |
| 62 | F | Cl | $CO_2H$ | $CH_3$ | H |
| 63 | F | Cl | $CO_2CH_3$ | $CH_3$ | H |
| 64 | F | Cl | $CO_2C_2H_5$ | $CH_3$ | H |
| 65 | F | Cl | $CO-SCH_3$ | $CH_3$ | H |
| 66 | F | Cl | $CO_2CH_2CH_2OCH_3$ | $CH_3$ | H |
| 67 | F | Cl | $CONH_2$ | $CH_3$ | H |
| 68 | F | Cl | $CONHCH_3$ | $CH_3$ | H |
| 69 | F | Cl | $CON(CH_3)_2$ | $CH_3$ | H |
| 70 | F | Cl | $CONHCH_2CH_2OCH_3$ | $CH_3$ | H |
| 71 | F | Cl | $CON(CH_3)CH_2CH_2OCH_3$ | $CH_3$ | H |
| 72 | F | Cl | $OCH(CH_3)_2$ | $CH_2C\equiv CH$ | H |
| 73 | F | Cl | $OCH(CH_3)_2$ | $NH_2$ | H |
| 74 | F | Cl | $OCH_2C\equiv CH$ | $CH_2CN$ | H |
| 75 | F | Cl | $NHCHCONHCHCH_3$<br>\| \|<br>$CH_3$ $C_2H_5$ | $CH_3$ | H |
| 76 | F | Cl | $OCHCONHCHCH_3$<br>\| \|<br>$CH_3$ $C_2H_5$ | $CH_3$ | H |
| 77 | F | Cl | $CH_3$ | $CH_3$ | H |
| 78 | F | Cl | 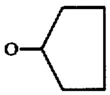 | $CH_3$ | H |
| 79 | F | Cl | $CF_3$ | $CH_3$ | H |
| 80 | F | Cl | SH | $CH_3$ | H |
| 81 | F | Cl | $SO_3H$ | $CH_3$ | H |
| 82 | F | Cl | $SCH_3$ | $CH_3$ | H |
| 83 | F | Cl | $SOCH_3$ | $CH_3$ | H |
| 84 | F | Cl | $SO_2CH_3$ | $CH_3$ | H |
| 85 | F | Cl | $SCH(CH_3)_2$ | $CH_3$ | H |
| 86 | F | Cl | $SCH_2C\equiv CH$ | $CH_3$ | H |
| 87 | F | Br | $NHCH(CH_3)CO_2C_2H_5$ | $CH_3$ | H |
| 88 | F | Cl | $NHCH(CH_3)CONHCH_3$ | $CH_3$ | H |
| 89 | F | Cl | $NHCH(CH_3)_2$ | $CH_3$ | H |
| 90 | F | Cl | $NHCH_2C\equiv CH$ | $CH_3$ | H |

TABLE 1-continued
Representative Compounds
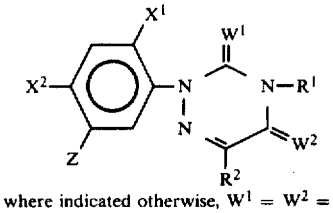
(Except where indicated otherwise, $W^1 = W^2 =$ oxygen).
| Compound Number | $X^1$ | $X^2$ | Z | $R^1$ | $R^2$ |
|---|---|---|---|---|---|
| 91 | F | Cl | 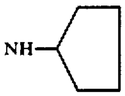 | $CH_3$ | H |
| 92 | F | Cl | $NHCOCH_3$ | $CH_3$ | H |
| 93 | F | Cl | $NHCO_2CH_3$ | $CH_3$ | H |
| 94 | F | Cl | 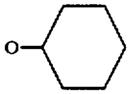 | $CH_3$ | H |
| 95 | F | Cl | $OCF_2H$ | $CH_3$ | H |
| 96 | F | Cl | $OCH_2OCH_3$ | $CH_3$ | H |
| 97 | F | Cl | 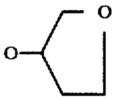 | $CH_3$ | H |
| 98 | F | Cl | 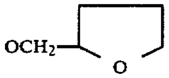 | $CH_3$ | H |
| 99 | F | Cl | 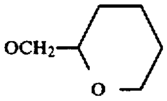 | $CH_3$ | H |
| 100 | F | Cl | 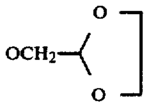 | $CH_3$ | H |
| 101 | F | Cl | 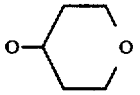 | $CH_3$ | H |
| 102 | F | Cl | 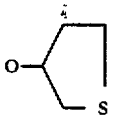 | $CH_3$ | H |
| 103 | F | Cl | 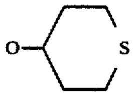 | $CH_3$ | H |
| 104 | F | Cl | 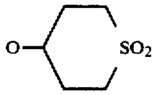 | $CH_3$ | H |

TABLE 1-continued

Representative Compounds

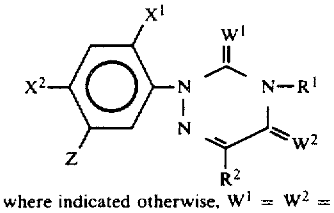

(Except where indicated otherwise, $W^1$ = $W^2$ = oxygen).

| Compound Number | $X^1$ | $X^2$ | Z | $R^1$ | $R^2$ |
|---|---|---|---|---|---|
| 105 | F | Cl | 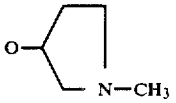 | $CH_3$ | H |
| 106 | F | Cl | 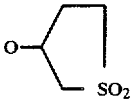 | $CH_3$ | H |
| 107 | F | Cl | $OSO_2N(CH_3)_2$ | $CH_3$ | H |
| 108 | F | Cl | $OSO_2C_6H_5$ | $CH_3$ | H |
| 109 | F | Cl | $OCH_2C{\equiv}CH$ | $CH_2(CH_2)_2F$ | H |
| 110 | F | Cl | $OCH_2C{\equiv}CH$ | $CH_2SO_2CH_3$ | H |
| 111 | F | Cl | $OCH_2C{\equiv}CH$ | $CH_2CH_2OCH_3$ | H |
| 112 | F | Cl | $OCH_2C{\equiv}CH$ | $CH_3$ | $C_2H_5$ |
| 113 | F | Cl | OH | H | H |
| 114[1] | F | Cl | $OCH(CH_3)_2$ | $CH_3$ | H |
| 115[2] | F | Cl | $OCH_2C{\equiv}CH$ | $CH_3$ | H |
| 116[2] | F | Cl | $OCH(CH_3)_2$ | $CH_3$ | H |
| 117[3] | F | Cl | $OCH_2C{\equiv}CH$ | $CH_3$ | H |
| 118[3] | F | Cl | $OCH(CH_3)_2$ | $CH_3$ | H |
| 119 | F | Cl | $OCH(CH_3)_2$ | $CH_2OCH_3$ | H |
| 120 | F | Cl | $OCH(CH_3)_2$ | $CH_3$ | H |
| 121 | F | $OCH_3$ | $OCH(CH_3)_2$ | $CH_3$ | H |
| 122 | F | Cl | $O{-}CH_2{-}$ 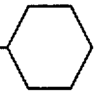 | $CH_3$ | H |
| 123 | F | Cl | 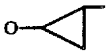 | $CH_3$ | H |
| 124 | F | Cl | $OCH_2SCH_3$ | $CH_3$ | H |
| 125 | F | Cl | $OCH_2CH{=}CH_2$ | $CH_3$ | H |
| 126 | F | Cl | $OCH_2C(Cl){=}CH_2$ | $CH_3$ | H |
| 127 | F | Cl | $O{-}CO{-}CH_3$ | $CH_3$ | H |
| 128 | F | Cl | $OCH_2CO_2H$ | $CH_3$ | H |
| 129 | F | Cl | $OCH_2CO_2CH_3$ | $CH_3$ | H |
| 130 | F | Cl | $OCH_2CO_2CH_2{-}$ 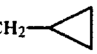 | $CH_3$ | H |
| 131 | F | Cl | $OCH_2CO_2CH_2{-}$ 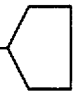 | $CH_3$ | H |
| 132 | F | Cl | $OCH_2CO_2CH_2{-}$ 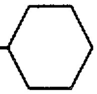 | $CH_3$ | H |
| 133 | F | Cl | $OCH_2CO_2{-}$ 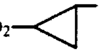 | $CH_3$ | H |

TABLE 1-continued

Representative Compounds

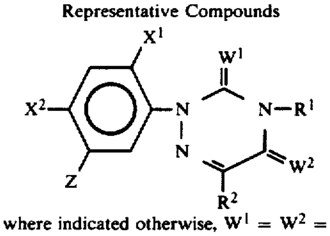

(Except where indicated otherwise, $W^1 = W^2$ = oxygen).

| Compound Number | $X^1$ | $X^2$ | Z | $R^1$ | $R^2$ |
|---|---|---|---|---|---|
| 134 | F | Cl | $OCH_2CO_2$— 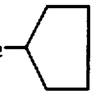 | $CH_3$ | H |
| 135 | F | Cl | $OCH_2CO_2$— 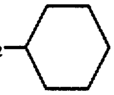 | $CH_3$ | H |
| 136 | F | Cl | $OCH_2CO_2$— 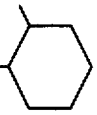 | $CH_3$ | H |
| 137 | F | Cl | $OCH_2CO_2—CH(CH_2)_5CH_2$ | $CH_3$ | H |
| 138 | F | Cl | $OCH_2CO—NH—CH_2OCH_3$ | $CH_3$ | H |
| 139 | F | Cl | $OCH_2CO—NH—CH_2SCH_3$ | $CH_3$ | H |
| 140 | F | Cl | $OCH_2CO_2CH_2CF_3$ | $CH_3$ | H |
| 141 | F | Cl | $OCH(CH_3)CO_2CH_2—CHCl_2$ | $CH_3$ | H |
| 142 | F | Cl | $OC(CH_3)_2CO_2CH_2—CH{=}CH_2$ | $CH_3$ | H |
| 143 | F | Cl | $OCH_2CO_2$— 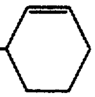 | $CH_3$ | H |
| 144 | F | Cl | $OCH_2CO_2CH_2$— 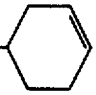 | $CH_3$ | H |
| 145 | F | Cl | $OCH_2CO_2C_6H_5$ | $CH_3$ | H |
| 146 | F | Cl | $OCH_2CO_2CH_2C_6H_5$ | $CH_3$ | H |
| 147 | F | Cl | $OCH(CH_3)CO_2CH_2CN$ | $CH_3$ | H |
| 148 | F | Cl | $OCH_2CO_2CH_2C{\equiv}CH$ | $CH_3$ | H |
| 149 | F | Cl | $OCH_2CO_2N{=}C(CH_3)_2$ | $CH_3$ | H |
| 150 | F | Cl | $OCH_2CO_2N{=}CH$— 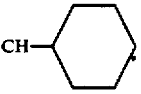 | $CH_3$ | H |
| 151 | F | Cl | $OCH_2CO_2N{=}$ 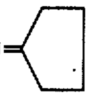 | $CH_3$ | H |
| 152 | F | Cl | $OCH_2CO_2N{=}$ 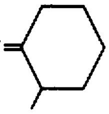 | H | H |
| 153[1] | F | Cl | $OCH(CH_3)_2$ | H | H |
| 154[2] | F | Cl | $OCH(CH_3)_2$ | H | H |
| 155[3] | F | Cl | $OCH(CH_3)_2$ | H | H |

TABLE 1-continued

Representative Compounds

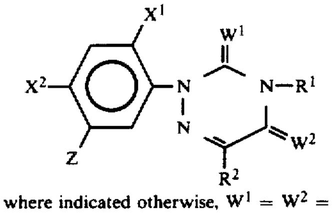

(Except where indicated otherwise, $W^1 = W^2$ = oxygen).

| Compound Number | $X^1$ | $X^2$ | Z | $R^1$ | $R^2$ |
|---|---|---|---|---|---|
| 156[1] | F | Cl | $OCH_2C{\equiv}CH$ | H | H |
| 157[2] | F | Cl | $OCH_2C{\equiv}CH$ | H | H |
| 158[3] | F | Cl | $OCH_2C{\equiv}CH$ | H | H |
| 159[1] | F | Cl | OH | H | H |
| 160[2] | F | Cl | OH | H | H |
| 161[3] | F | Cl | OH | H | H |
| 162[1] | F | Cl | OH | $CH_3$ | H |
| 163[2] | F | Cl | OH | $CH_3$ | H |
| 164[3] | F | Cl | OH | $CH_3$ | H |
| 165[1] | F | Cl | $OCH(CH_3)_2$ | H | $CO_2H$ |
| 166[2] | F | Cl | $OCH(CH_3)_2$ | H | $CO_2H$ |
| 167[3] | F | Cl | $OCH(CH_3)_2$ | H | $CO_2H$ |
| 168[1] | F | Cl | $OCH_2C{\equiv}CH$ | H | $CO_2H$ |
| 169[2] | F | Cl | $OCH_2C{\equiv}CH$ | H | $CO_2H$ |
| 170[3] | F | Cl | $OCH_2C{\equiv}CH$ | H | $CO_2H$ |
| 171[1] | F | Cl | $OCH(CH_3)_2$ | $CH_3$ | $CO_2H$ |
| 172[2] | F | Cl | $OCH(CH_3)_2$ | $CH_3$ | $CO_2H$ |
| 173[3] | F | Cl | $OCH(CH_3)_2$ | $CH_3$ | $CO_2H$ |
| 174[1] | F | Cl | $OCH_2C{\equiv}CH$ | $CH_3$ | $CO_2H$ |
| 175[2] | F | Cl | $OCH_2C{\equiv}CH$ | $CH_3$ | $CO_2H$ |
| 176[3] | F | Cl | $OCH_2C{\equiv}CH$ | $CH_3$ | $CO_2H$ |
| 177 | F | Cl | $OCH_2C{\equiv}CH$ | H | H |
| 178 | F | Cl | $OCH(CH_3)_2$ | H | $CO_2H$ |
| 179 | F | Cl | $OCH_2C{\equiv}CH$ | H | $CO_2H$ |
| 180 | F | Cl | $OCH(CH_3)_2$ | $CH_3$ | $CO_2H$ |
| 181 | F | Cl | $OCH_2C{\equiv}CH$ | $CH_3$ | $CO_2H$ |
| 182[1] | F | Cl | $OCH(CH_3)_2$ | $CH_3$ | H |
| 183 | F | Cl | $OCH(CH_3)_2$ | $CH_2CH_2CH_3$ | H |
| 184 | F | Cl | $OCH(CH_3)_2$ | $CH_2CH_2F$ | H |
| 185 | F | Cl | $OCH(CH_3)_2$ | $CH_2(CH_2)_2CH_3$ | H |
| 186 | Cl | Cl | $NH_2$ | $CH_3$ | H |
| 187 | Cl | Cl | $N(COCH_3)_2$ | $CH_3$ | H |
| 188 | Cl | Cl | Cl | $CH_3$ | H |
| 189 | F | Cl | I | $CH_3$ | H |
| 190 | F | Cl | Cl | $CH_3$ | H |
| 191 | F | Cl | $OCSN(CH_2CH_3)_2$ | $CH_3$ | H |
| 192 | F | Cl | $SCON(CH_2CH_3)_2$ | $CH_3$ | H |
| 193 | F | Cl | $OCH(CH_3)CO_2C(CH_3)_3$ | $CH_3$ | H |
| 194 | F | Cl | $NHN{=}C(CH_3)_2$ | $CH_3$ | H |
| 195 | F | Cl | $OCH_2OCH_2CH_2OCH_3$ | $CH_3$ | H |
| 196 | F | Cl | $OCH(CH_3)_2$ | $CH_2SCH_3$ | H |
| 197 | F | Cl | $OCH(CH_3)_2$ | $CH_2SOCH_3$ | H |
| 198 | F | Cl | $OCH(CH_3)CO_2H$ | $CH_3$ | H |
| 199[1] | F | Br | $OCH(CH_3)_2$ | $CH_3$ | H |
| 200 | F | Cl | $O(CH_2)_2CH_3$ | $CH_3$ | H |
| 201 | F | Cl | $O(CH_2)_2CH{=}CH_2$ | $CH_3$ | H |
| 202 | F | Cl | $OCH_2CN$ | $CH_3$ | H |
| 203[1] | F | Br | $OCH_2C{\equiv}CH$ | $CH_3$ | H |
| 204[2] | F | Br | $OCH_2C{\equiv}CH$ | $CH_3$ | H |
| 205[3] | F | Br | $OCH_2C{\equiv}CH$ | $CH_3$ | H |
| 206 | F | Cl | $NHCH(CH_2)_4CH$ | $CH_3$ | H |
| 207 | F | Cl | $OCH(CH_3)CO_2CH(CH_3)_2$ | $CH_3$ | H |
| 208 | F | Cl | $OCH(CH_3)CO{-}SC_2H_5$ | $CH_3$ | H |
| 209 | F | Cl | 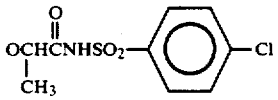 | $CH_3$ | H |

TABLE 1-continued

Representative Compounds

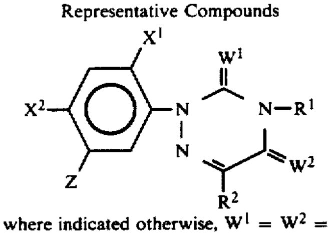

(Except where indicated otherwise, $W^1 = W^2 =$ oxygen).

| Compound Number | $X^1$ | $X^2$ | Z | $R^1$ | $R^2$ |
|---|---|---|---|---|---|
| 210 | F | Cl | 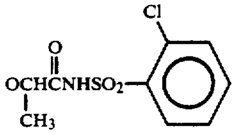 | $CH_3$ | H |
| 211 | F | Cl | $OCH_3$ | $CH_3$ | H |
| 212 | F | Cl | $OCH_2SOCH_3$ | $CH_3$ | H |
| 213 | F | Cl | $OCH_2SO_2CH_3$ | $CH_3$ | H |
| 214 | F | Cl | F | H | H |
| 215 | F | Cl | F | $CH_3$ | H |
| 216[2] | F | Br | $OCH(CH_3)_2$ | $CH_3$ | H |
| 217[3] | F | Br | $OCH(CH_3)_2$ | $CH_3$ | H |
| 218 | F | Cl | $SO_2Cl$ | $CH_3$ | H |
| 219 | F | Cl | 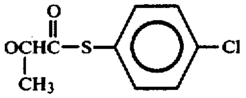 | $CH_3$ | H |
| 220 | F | Cl | $OCH(OC_2H_5)CO_2C_2H_5$ | $CH_3$ | H |
| 221 | F | Cl | $OCH(OCH_3)CO_2CH_3$ | $CH_3$ | H |
| 222 | F | Cl | 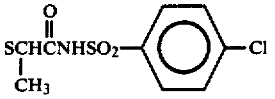 | $CH_3$ | H |
| 223 | F | Cl | $SCH(CH_3)CO_2CH(CH_3)_2$ | $CH_3$ | H |
| 224 | F | Cl | $SCH(CH_2)_3CH$ | $CH_3$ | H |
| 225 | F | Cl | $SCH_2OCH_3$ | $CH_3$ | H |
| 226 | F | Cl | $SCH_2CN$ | $CH_3$ | H |
| 227 | F | Br | $OCH_2C{\equiv}CH$ | $CH_3$ | H |
| 228 | F | Cl | 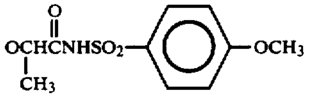 | $CH_3$ | H |
| 229 | F | Cl | $OCH_2Si(CH_3)_3$ | $CH_3$ | H |
| 230 | F | Cl | $OC_2H_5$ | $CH_3$ | H |
| 231 | F | Cl | 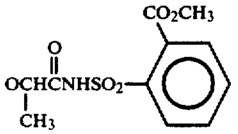 | $CH_3$ | H |
| 232 | F | Cl | $NHCH(CH_3)CO_2C_2H_5$ | $CH_3$ | H |
| 233 | F | Br | $OCH(CH_3)CO_2CH(CH_3)_2$ | $CH_3$ | H |
| 234 | F | Br | $OCH_2OCH_3$ | $CH_3$ | H |
| 235 | F | Br | 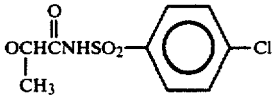 | $CH_3$ | H |
| 236 | F | Cl | $O(CH_2)_2F$ | $CH_3$ | H |

TABLE 1-continued

Representative Compounds

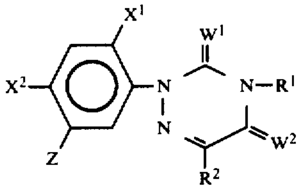

(Except where indicated otherwise, $W^1$ = $W^2$ = oxygen).

| Compound Number | $X^1$ | $X^2$ | Z | $R^1$ | $R^2$ |
|---|---|---|---|---|---|
| 237 | F | Cl | $OCH_2CF_3$ | $CH_3$ | H |
| 238 | F | Cl | 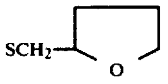 | $CH_3$ | H |
| 239 | F | Cl | $OCH_2C{\equiv}CH$ | $CHF_3$ | H |
| 240 | F | Br | H | $CH_3$ | H |
| 241[1] | F | Br | H | $CH_3$ | H |
| 242[2] | F | Cl | H | $CH_3$ | H |
| 243 | F | Cl | $OC(CH_3)_2CO_2C_2H_5$ | $CH_3$ | H |
| 244 | F | Cl | 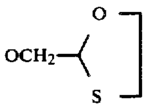 | $CH_3$ | H |
| 245 | F | Cl | CN | $CH_3$ | H |
| 246 | F | Cl | $CH_3$ | $CH_3$ | H |
| 247 | F | Cl | $CF_3$ | $CH_3$ | H |
| 248 | F | Cl | $CO_2Na$ | $CH_3$ | H |
| 249 | F | Cl | $SO_3Na$ | $CH_3$ | H |
| 250 | F | Br | $OCH(CH_3)CO_2Na$ | $CH_3$ | H |
| 251 | F | Cl | 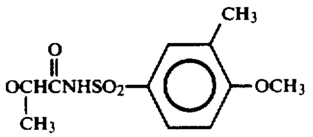 | $CH_3$ | H |
| 252 | F | Cl | 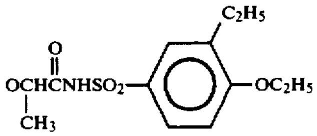 | $CH_3$ | H |
| 253 | F | Cl | 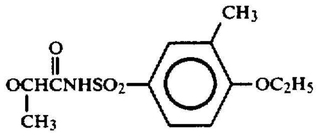 | $CH_3$ | H |
| 254 | F | Cl | 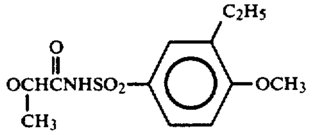 | $CH_3$ | H |
| 255 | F | Br | 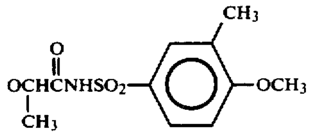 | $CH_3$ | H |

TABLE 1-continued

Representative Compounds

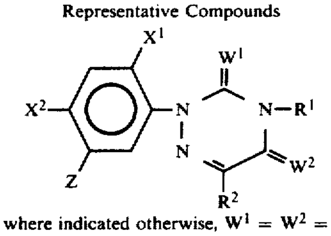

(Except where indicated otherwise, $W^1$ = $W^2$ = oxygen).

| Compound Number | $X^1$ | $X^2$ | Z | $R^1$ | $R^2$ |
|---|---|---|---|---|---|
| 256 | F | $CF_3$ | 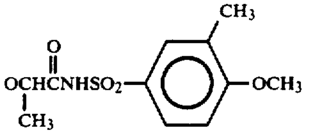 | $CH_3$ | H |

[1]$W^1$ = O, $W^2$ = S
[2]$W^1$ = S, $W^2$ = O
[3]$W^1$ = $W^2$ = S
[4]$X^1$ = 3-Cl

TABLE 2

| Compound Number | M.P. (°C.) | Empirical Formula | Characterizing Data Elemental Analysis | C | H | N |
|---|---|---|---|---|---|---|
| 1 | 79-81 | $C_{10}H_9N_3O_2$ | | | | |
| 2 | oil | $C_{10}H_8FN_3O_2$/ | C | 53.22 | 3.80 | 18.62 |
| | | 0.25 $H_2O$ | F | 53.55 | 3.48 | 18.09 |
| 3 | 99-100 | $C_{12}H_{10}ClN_3O_2$ | C | 54.66 | 3.82 | 15.94 |
| | | | F | 54.63 | 3.57 | 16.15 |
| 4 | 197(d) | $C_{10}H_7Cl_2N_3O_2$ | | | | |
| 5 | 109-110 | $C_{11}H_9Cl_2N_3O_2$ | | | | |
| 6 | 202-203 | $C_9H_5ClFN_3O_2$ | | | | |
| 7 | 114-116 | $C_{10}H_7ClFN_3O_2$ | | | | |
| 8 | 167-168 | $C_{10}H_7Cl_2N_3O_2$ | C | 44.14 | 2.59 | 15.44 |
| | | | F | 43.85 | 2.40 | 15.22 |
| 9 | 199-201 | $C_{10}H_7Cl_2N_3O_3$ | | | | |
| 10 | 163-164 | $C_{13}H_{13}Cl_2N_3O_3$ | C | 47.29 | 3.97 | 12.73 |
| | | | F | 47.47 | 3.82 | 12.33 |
| 11 | 195-197 | $C_{13}H_{11}Cl_2N_3O_5$/ | C | 42.30 | 3.28 | 11.38 |
| | (d) | 0.5 $H_2O$ | F | 42.38 | 3.31 | 11.75 |
| 12 | 111-112 | $C_{13}H_{13}Cl_2N_3O_3$ | C | 47.29 | 3.97 | 12.73 |
| | | | F | 47.18 | 4.03 | 12.43 |
| 13 | oily solid | $C_{14}H_{15}Cl_2N_3O_3$ | | | | |
| 14 | 230(d) | $C_{14}H_{13}Cl_2N_3O_3$ | | | | |
| 15 | 103-104 | $C_{15}H_{15}Cl_2N_3O_3$ | C | 50.58 | 4.24 | 11.80 |
| | | | F | 50.30 | 4.25 | 11.52 |
| 16 | 74-75 | $C_{16}H_{17}Cl_2N_3O_3$ | | | | |
| 17 | oil | $C_{12}H_{11}ClFN_3O_3$ | | | | |
| 18 | 82-84 | $C_{13}H_{13}ClFN_3O_3$ | | | | |
| 19 | 84-86 | $C_{15}H_{15}ClFN_3O_3$ | | | | |
| 20 | 119-120 | $C_{13}H_9Cl_2N_3O_3$ | | | | |
| 21 | 122-123 | $C_{13}H_9ClFN_3O_3$ | | | | |
| 22 | 115-117 | $C_{14}H_{13}Cl_2N_3O_5$ | | | | |
| 23 | oil | $C_{11}H_9Cl_2N_3O_5S$ | C | 36.08 | 2.48 | 11.48 |
| | | | F | 36.99 | 2.70 | 10.85 |
| 24 | 134-135 | $C_{13}H_9ClFN_3O_3S$ | | | | |
| 25 | 142-144 | $C_{15}H_{13}Cl_2N_3O_2$ | C | 50.87 | 3.70 | 11.86 |
| | | | F | 50.37 | 3.95 | 11.66 |
| 26 | oil | $C_{13}H_{14}Cl_2FN_3O_3$ | C | 46.43 | 3.90 | 11.60 |
| | | | F | 46.45 | 3.66 | 11.48 |
| 27 | 108-110 | $C_{15}H_{15}Cl_2N_3O_5$ | C | 46.41 | 3.89 | 10.82 |
| | | | F | 46.14 | 3.70 | 10.65 |
| 28 | 169-170 | $C_{12}H_8Cl_2N_4O_3$ | C | 43.46 | 2.58 | 16.95 |
| | | | F | 43.27 | 2.36 | 16.69 |
| 29 | 82-83 | $C_{14}H_{15}Cl_2N_3O_3$ | C | 48.86 | 4.39 | 12.21 |
| | | | F | 49.25 | 4.22 | 12.15 |
| 30 | 183(d) | $C_{10}H_7ClFN_3O_3$ | | | | |
| 31 | 155(d) | $C_{10}H_6ClN_3O_4$ | | | | |
| 32 | 157(d) | $C_{11}H_8ClN_3O_5$ | C | 48.34 | 2.70 | 18.79 |
| | | | F | 48.32 | 2.81 | 18.51 |
| 33 | 229-230 | $C_9H_6ClN_3O_2$ | C | 57.82 | 4.61 | 20.23 |
| | | | F | 58.11 | 4.50 | 19.73 |
| 34 | 200-202 | $C_{10}H_9N_3O_2$/ | C | 60.82 | 5.10 | 19.34 |

TABLE 2-continued

| Compound Number | M.P. (°C.) | Empirical Formula | Characterizing Data Elemental Analysis | C | H | N |
|---|---|---|---|---|---|---|
| | | 0.25 $H_2O$ | F | 61.35 | 5.40 | 19.85 |
| 35 | 136-137 | $C_{11}H_{11}N_3O_2$ | C | 50.54 | 3.39 | 17.68 |
| | | | F | 50.70 | 3.66 | 17.92 |
| 36 | 152-154 | $C_{10}H_8ClN_3O_2$ | C | 43.48 | 3.83 | 15.22 |
| | | | F | 43.61 | 3.28 | 13.10 |
| 37 | 170-173 | $C_{10}H_8ClN_3O_3$/ | C | 50.63 | 4.67 | 17.71 |
| | | 1.25 $H_2O$ | F | 50.12 | 3.85 | 16.14 |
| 38 | 192(d) | $C_{10}H_9N_3O_3/H_2O$ | C | 48.54 | 3.89 | 15.44 |
| | | | F | 48.47 | 3.71 | 14.10 |
| 39 | 108-110 | $C_{11}H_{10}ClN_3O_3$/ | C | 56.65 | 4.75 | 18.01 |
| | | 0.25 $H_2O$ | F | 56.26 | 4.55 | 17.66 |
| 40 | 114-116 | $C_{11}H_{11}N_3O_3$ | C | 47.07 | 3.65 | 12.67 |
| | | | F | 47.20 | 3.77 | 12.22 |
| 41 | 111-113 | $C_{13}H_{12}ClF_2N_3O_3$ | C | 47.01 | 3.66 | 11.75 |
| | | | F | 46.51 | 3.69 | 11.31 |
| 42 | 100-102 | $C_{14}H_{13}ClFN_3O_5$ | | | | |
| 43 | oil | $C_{14}H_{13}ClFN_3O_5$ | | | | |
| 44 | oil | $C_{13}H_8ClF_2N_3O_3$ | C | 47.65 | 2.46 | 12.82 |
| | | | F | 48.10 | 2.58 | 12.03 |
| 45 | oil | $C_{14}H_{12}ClFN_4O_3$ | C | 49.64 | 3.57 | 16.54 |
| | | | F | 49.44 | 3.90 | 14.65 |
| 46 | 132-134 | $C_{10}H_6ClFN_4O_4$ | C | 39.95 | 2.01 | 18.64 |
| | | | F | 40.22 | 1.98 | 18.51 |
| 47 | 150-152 | $C_{10}H_8ClFN_4O_2$ | C | 44.38 | 2.98 | 20.70 |
| | | | F | 44.30 | 3.29 | 20.40 |
| 48 | 127-129 | $C_{13}H_8BrClFN_3O_3$ | | | | |
| 49 | 208(d) | $C_{12}H_{10}ClFN_4O_4$ | | | | |
| 50 | 70-71 | $C_{15}H_{16}ClF_2N_3O_3$ | C | 50.08 | 4.48 | 11.68 |
| | | | F | 50.26 | 4.45 | 12.00 |
| 53 | 89-92 | $C_{13}H_{13}BrFN_3O_3$ | C | 43.59 | 3.66 | 11.73 |
| | | | F | 43.47 | 3.40 | 11.72 |
| 55 | oil | $C_{14}H_{16}FN_3O_3$ | | | | |
| 74 | oil | $C_{14}H_8ClFN_4O_3$ | | | | |
| 75 | 194-197 | $C_{17}H_{21}ClFN_5O_3$ | | | | |
| 76 | 155-156 | $C_{17}H_{20}ClFN_4O_4$ | C | 51.20 | 5.05 | 14.05 |
| | | | F | 51.20 | 5.19 | 14.22 |
| 77 | 138-139 | $C_{11}H_9ClFN_3O_2$ | C | 40.99 | 3.36 | 15.58 |
| | | | F | 40.88 | 2.90 | 13.65 |
| 78 | 122-123 | $C_{15}H_{15}ClFN_3O_3$ | | | | |
| 82 | 128-131 | $C_{11}H_9ClFN_3O_2S$ | | | | |
| 85 | 95-97 | $C_{13}H_{13}ClFN_3O_2S$ | | | | |
| 86 | foam | $C_{13}H_9ClFN_3O_2S$ | | | | |
| 89 | solid | $C_{13}H_{14}ClFN_4O_2$ | C | 49.93 | 4.51 | 17.92 |
| | | | F | 50.55 | 4.55 | 17.31 |
| 96 | 109-111 | $C_{12}H_{11}ClFN_3O_4$ | C | 45.66 | 3.51 | 13.31 |
| | | | F | 45.45 | 3.35 | 12.92 |
| 113 | >225 | $C_9H_5ClFN_3O_3$ | C | 41.96 | 1.96 | 16.31 |
| | | | F | 43.20 | 2.54 | 14.69 |
| 114 | 80-81 | $C_{13}H_{12}ClFN_3O_2S$ | C | 47.35 | 3.97 | 12.74 |

TABLE 2-continued

| Compound Number | M.P. (°C.) | Empirical Formula | | Characterizing Data Elemental Analysis C | H | N |
|---|---|---|---|---|---|---|
| | | | F | 47.71 | 4.05 | 12.69 |
| 119 | 100–102 | $C_{14}H_{15}ClFN_3O_4$ | C | 48.92 | 4.40 | 12.22 |
| | | | F | 49.09 | 4.32 | 11.95 |
| 124 | oil | $C_{12}H_{11}ClFN_3O_3S$ | C | 43.46 | 3.34 | 12.67 |
| | | | F | 43.89 | 3.46 | 12.12 |
| 125 | oil | $C_{13}H_{11}ClFN_3O_3$ | C | 50.09 | 3.56 | 13.48 |
| | | | F | 50.16 | 3.73 | 13.00 |
| 182 | 134–135 | $C_{13}H_9ClFN_3O_2S$ | | | | |
| 183 | 61–63 | $C_{15}H_{17}ClFN_3O_3$ | C | 52.72 | 5.01 | 12.29 |
| | | | F | 52.55 | 4.95 | 11.53 |
| 184 | oil | $C_{14}H_{14}ClF_2N_3O_3$ | C | 48.64 | 4.08 | 12.15 |
| | | | F | 47.88 | 3.81 | 11.68 |
| 185 | 73–74 | $C_{16}H_{19}ClFN_3O_3$ | C | 54.01 | 5.38 | 11.81 |
| | | | F | 54.55 | 5.59 | 11.40 |
| 186 | 168–171 | $C_{10}H_8Cl_2N_4O_2$ | | | | |
| 187 | foam | $C_{14}H_{12}Cl_2N_4O_4$/ 0.5 $H_2O$ | C | 44.23 | 3.45 | 14.73 |
| | | | F | 44.15 | 3.15 | 14.44 |
| 188 | 172–173 | $C_{10}H_6Cl_3N_3O_2$ | C | 39.18 | 1.97 | 13.71 |
| | | | F | 39.83 | 2.35 | 13.55 |
| 189 | 182–185 | $C_{10}H_6ClFIN_3O_2$ | C | 31.48 | 1.59 | 11.01 |
| | | | F | 33.48 | 1.83 | 11.59 |
| 190 | 140–142 | $C_{10}H_6Cl_2FN_3O_2$ | C | 41.41 | 2.08 | 14.49 |
| | | | F | 41.65 | 2.13 | 14.05 |
| 191 | 120–121 | $C_{15}H_{16}ClFN_4O_3S$ | C | 46.57 | 4.17 | 14.48 |
| | | | F | 46.47 | 4.02 | 14.29 |
| 192 | 156–157 | $C_{15}H_{16}ClFN_4O_3S$ | C | 46.57 | 4.17 | 14.48 |
| | | | F | 46.66 | 4.14 | 14.37 |
| 193 | 86–88 | $C_{17}H_{19}ClFN_3O_4$ | C | 50.94 | 5.03 | 10.48 |
| | | | F | 51.13 | 4.75 | 10.35 |
| 194 | 146–147 | $C_{13}H_{13}ClFN_5O_2$ | C | 47.94 | 4.02 | 21.50 |
| | | | F | 48.20 | 3.77 | 21.46 |
| 195 | oil | $C_{14}H_{15}ClFN_3O_5$/ 0.5 $H_2O$ | C | 45.60 | 4.37 | 11.39 |
| | | | F | 45.67 | 4.07 | 11.20 |
| 196 | 95–97 | $C_{14}H_{15}ClFN_3O_3S$ | C | 46.73 | 4.20 | 11.68 |
| | | | F | 46.76 | 4.24 | 11.39 |
| 197 | 138–140 | $C_{14}H_{15}ClFN_3O_4S$ | C | 44.74 | 4.02 | 11.18 |
| | | | F | 44.15 | 3.78 | 10.99 |
| 198 | 123–125 | $C_{13}H_{11}ClFN_3O_5$ | C | 45.43 | 3.23 | 12.23 |
| | | | F | 45.14 | 3.23 | 11.95 |
| 200 | 88–89 | $C_{13}H_{13}ClFN_3O_3$ | C | 49.77 | 4.18 | 13.39 |
| | | | F | 49.74 | 4.07 | 13.34 |
| 201 | oil | $C_{14}H_{13}ClFN_3O_3$ | C | 51.62 | 4.02 | 12.90 |
| | | | F | 51.32 | 4.04 | 12.50 |
| 202 | 153–155 | $C_{12}H_8ClFN_4O_3$ | C | 46.39 | 2.60 | 18.03 |
| | | | F | 46.08 | 2.49 | 17.81 |

TABLE 2-continued

| Compound Number | M.P. (°C.) | Empirical Formula | | Characterizing Data Elemental Analysis C | H | N |
|---|---|---|---|---|---|---|
| 206 | gum | $C_{16}H_{18}ClFN_4O_2$ | C | 54.47 | 5.14 | 15.83 |
| | | | F | 55.83 | 4.80 | 15.36 |
| 207 | oil | $C_{16}H_{17}ClFN_3O_5$ | C | 49.82 | 4.44 | 10.89 |
| | | | F | 47.82 | 4.31 | 10.22 |
| 208 | oil | $C_{15}H_{15}ClFN_3O_4S$ | C | 44.75 | 4.02 | 11.18 |
| | | | F | 44.72 | 3.71 | 10.06 |
| 209 | 97(d) | $C_{19}H_{15}Cl_2FN_4O_6S$/ $H_2O$ | C | 42.63 | 3.20 | 10.46 |
| | | | F | 42.61 | 4.06 | 9.44 |
| 210 | solid | $C_{19}H_{15}Cl_2FN_4O_6S$/ $H_2O$ | C | 42.63 | 3.20 | 10.46 |
| | | | F | 42.73 | 4.27 | 9.33 |
| 211 | 145–146 | $C_{11}H_9ClFN_3O_3$ | C | 46.25 | 3.18 | 14.71 |
| | | | F | 45.90 | 2.80 | 14.46 |
| 212 | 164–166 | $C_{12}H_{11}ClFN_3O_4S$ | C | 41.45 | 3.19 | 12.08 |
| | | | F | 41.45 | 3.07 | 11.67 |
| 213 | 154–156 | $C_{12}H_{11}ClFN_3O_5S$ | C | 39.62 | 3.05 | 11.55 |
| | | | F | 39.30 | 3.15 | 11.13 |
| 214 | 233–234 | $C_9H_4ClF_2N_3O_2$ | C | 41.64 | 1.55 | 16.19 |
| | | | F | 41.50 | 1.78 | 15.76 |
| 215 | 110–111 | $C_{10}H_6ClF_2N_3O_2$ | C | 43.90 | 2.21 | 15.36 |
| | | | F | 43.64 | 2.13 | 15.21 |
| 218 | 123–125 | $C_{10}H_6Cl_2FN_3O_4S$ | C | 33.92 | 1.71 | 11.87 |
| | | | F | 34.11 | 1.79 | 11.78 |
| 219 | solid | $C_{19}H_{14}Cl_2FN_3O_4S$ | | | | |
| 220 | oil | $C_{16}H_{17}ClFN_3O_6$ | C | 47.83 | 4.27 | 10.46 |
| | | | F | 47.93 | 4.13 | 10.18 |
| 221 | oil | $C_{14}H_{13}ClFN_3O_6$ | | | | |
| 222 | 110(d) | $C_{19}H_{15}Cl_2FN_4O_5S_2$ | | | | |
| 223 | oil | $C_{16}H_{17}ClFN_3O_4S$ | C | 47.82 | 4.26 | 10.46 |
| | | | F | 46.14 | 4.10 | 10.04 |
| 224 | 51–53 | $C_{15}H_{15}ClFN_3O_2S$ | | | | |
| 225 | 95–98 | $C_{12}H_{11}ClFN_3O_2S$ | | | | |
| 226 | 123–125 | $C_{12}H_8ClFN_4O_2S$ | | | | |
| 227 | 123–124 | $C_{13}H_9BrFN_3O_3$ | C | 44.09 | 2.56 | 11.87 |
| | | | F | 44.40 | 2.35 | 11.42 |
| 228 | 195–196 | $C_{20}H_{18}ClFN_4O_7S$ | C | 46.83 | 3.53 | 10.92 |
| | | | F | 46.94 | 3.80 | 10.39 |
| 229 | 125–126 | $C_{14}H_{17}ClFN_3O_3Si$ | C | 46.99 | 4.79 | 11.74 |
| | | | F | 47.26 | 4.62 | 11.65 |
| 230 | solid | $C_{12}H_{11}ClFN_3O_3$ | | | | |
| 231 | solid | $C_{21}H_{18}ClFN_4O_8S$ | C | 46.72 | 3.17 | 10.38 |
| | | | F | 44.35 | 3.72 | 7.43 |
| 232 | oil | $C_{15}H_{16}ClFN_4O_4$/ 1.5 $H_2O$ | C | 45.29 | 4.81 | 14.08 |
| | | | F | 45.40 | 4.63 | 13.65 |
| 233 | gum | $C_{16}H_{17}BrFN_3O_3$ | C | 44.67 | 3.98 | 9.77 |
| | | | F | 44.35 | 3.93 | 9.44 |
| 234 | 79–81 | $C_{12}H_{11}BrFN_3O_4$ | C | 40.02 | 3.08 | 11.68 |
| | | | F | 39.86 | 2.91 | 11.29 |
| 235 | 120(d) | $C_{19}H_{15}BrClFN_4O_6S$/ $H_2O$ | C | 39.36 | 2.96 | 9.66 |
| | | | F | 39.62 | 2.78 | 8.49 |
| 236 | 134–136 | $C_{12}H_{10}ClF_2N_3O_3$ | C | 45.37 | 3.17 | 13.23 |
| | | | F | 44.88 | 2.86 | 12.87 |
| 237 | gum | $C_{12}H_8ClF_4N_3O_3$ | C | 40.75 | 2.28 | 11.88 |
| | | | F | 40.51 | 2.26 | 11.16 |

TABLE 3

Preemergence Herbicidal Activity

| Compound No. | 1 | 2 | 3 | 4 | 5 | 6 | 7 | 8 | 9 | 10 | 11 | 12 | 13 | 15 | 16 | 17 | 18 | 19 | 20 | 21 | 22 | 23 | 24 | 25 | 26 | 27 | 28 | 29 | 30 |
|---|---|---|---|---|---|---|---|---|---|---|---|---|---|---|---|---|---|---|---|---|---|---|---|---|---|---|---|---|---|
| Rate (kg/ha) | 8.0 | 8.0 | 8.0 | 8.0 | 8.0 | 8.0 | 8.0 | 8.0 | 8.0 | 8.0 | 8.0 | 8.0 | 4.0 | 8.0 | 8.0 | 8.0 | 8.0 | 8.0 | 8.0 | 2.0 | 8.0 | 8.0 | 0.5 | 8.0 | 8.0 | 4.0 | 4.0 | 8.0 | 8.0 |
| Species | % K | % C | % K | % C | % C | % C | % C | % K | % K | % K | % K | % K | % K | % K | % K | % K | % C | % C | % C | % C | % C | % C | % C | % C | % C | % C | % C | % C | % C |
| Cotton | 0 | 90 | 90 | 0 | 0 | 10 | 100 | 0 | 20 | 0 | 0 | 10 | 0 | 0 | 0 | 0 | 100 | 80 | 100 | 100 | 100 | 90 | 100 | 0 | 20 | 90 | 50 | 60 | 100 |
| Soybean | 0 | 90 | 90 | 0 | 0 | 50 | 100 | 0 | 0 | 0 | 0 | 100 | 40 | 10 | 0 | 10 | 100 | 90 | 100 | 100 | 100 | 90 | 100 | 0 | 40 | 30 | 50 | 90 | 100 |
| Field Corn | 0 | 70 | 100 | 0 | 0 | 50 | 100 | 0 | 0 | 0 | 0 | 70 | 60 | 0 | 0 | 33 | 100 | 100 | 100 | 100 | 90 | 100 | 100 | 0 | 90 | 80 | 100 | 90 | 100 |
| Wheat | 0 | 80 | 100 | 0 | 0 | 50 | 100 | 10 | 10 | 0 | 0 | 100 | 40 | 20 | 0 | 0 | 100 | 100 | 100 | 100 | 0 | 100 | 100 | 20 | 90 | 30 | 70 | 60 | 100 |
| Field Bindweed | 0 | 90 | 100 | 0 | 0 | 50 | 100 | 20 | 0 | 0 | 0 | 100 | 50 | 0 | 100 | 0 | 100 | 100 | 100 | 100 | 100 | 80 | 100 | 0 | 70 | 100 | 10 | 90 | 100 |
| Morningglory | 30 | 90 | 90 | 0 | 0 | 30 | 100 | 50 | 10 | 0 | 0 | 100 | 0 | 0 | 80 | 0 | 100 | 100 | 100 | 100 | 70 | 90 | 90 | 20 | 50 | 40 | 50 | 70 | 100 |
| Velvetleaf | — | 90 | — | 0 | 0 | 100 | 100 | — | 0 | 100 | 0 | 100 | 100 | 100 | 0 | — | 100 | — | 100 | 100 | 90 | 100 | 100 | 0 | 100 | 100 | 100 | 100 | 100 |
| Barnyardgrass | 0 | 90 | 100 | 0 | 0 | 20 | 100 | 80 | 10 | 0 | 0 | 100 | 100 | 30 | 0 | 0 | 100 | 100 | 100 | 100 | 90 | 100 | 100 | 80 | 80 | 100 | 100 | 100 | 100 |
| Green Foxtail | 0 | 100 | — | 0 | 0 | 90 | 100 | — | — | 100 | 0 | 100 | — | 100 | 95 | — | — | — | 100 | 100 | 90 | 100 | 100 | 90 | 100 | 100 | 100 | 100 | 100 |
| Johnsongrass | 30 | 80 | 100 | 0 | 0 | 80 | 100 | 90 | 10 | 0 | 0 | 100 | 100 | 30 | 0 | 0 | 100 | 100 | 100 | 100 | 80 | 100 | 100 | 80 | 90 | 100 | 80 | 100 | 100 |

| Compound No. | 31 | 32 | 33 | 34 | 35 | 36 | 37 | 38 | 39 | 40 | 41 | 42 | 43 | 44 | 45 | 46 | 47 | 48 | 49 | 50 | 53 | 55 | 73 | 75 | 76 | 77 | 78 | 82 | 85 |
|---|---|---|---|---|---|---|---|---|---|---|---|---|---|---|---|---|---|---|---|---|---|---|---|---|---|---|---|---|---|
| Rate (kg/ha) | 8.0 | 8.0 | 8.0 | 8.0 | 8.0 | 4.0 | 8.0 | 8.0 | 8.0 | 8.0 | 0.5 | 1.0 | 1.0 | 0.5 | 4.0 | 4.0 | 4.0 | 0.25 | 2.0 | 2.0 | 0.25 | 0.5 | 4.0 | 1.0 | 1.0 | 1.0 | 1.0 | 2.0 | 0.5 |
| Species | % C | % C | % C | % C | % C | % C | % C | % C | % C | % C | % C | % C | % C | % C | % C | % C | % C | % C | % C | % C | % C | % C | % C | % C | % C | % C | % C | % C | % C |
| Cotton | 0 | 0 | 40 | 0 | 90 | 90 | 0 | 0 | 20 | 90 | 50 | 100 | 40 | 100 | 100 | 10 | 10 | 0 | 100 | 80 | 0 | 30 | 40 | 100 | 90 | 100 | 30 | 100 | 30 |
| Soybean | 0 | 0 | 40 | 0 | 80 | 90 | 70 | 0 | 50 | 90 | 90 | 100 | 70 | 100 | 100 | 90 | 100 | 0 | 100 | 50 | 10 | 20 | 50 | 100 | 80 | 100 | 100 | 100 | 30 |
| Field Corn | 0 | 0 | 30 | 0 | 80 | 100 | 20 | 0 | 60 | 100 | 90 | 30 | 60 | 100 | 100 | 10 | 30 | 50 | 100 | 90 | 95 | 90 | 40 | 100 | 100 | 100 | 80 | 100 | 90 |
| Wheat | 0 | 0 | 0 | 0 | 70 | 100 | 0 | 0 | 10 | 90 | 100 | 60 | 0 | 100 | 100 | 10 | 30 | 0 | 20 | 100 | 100 | 0 | 90 | 100 | 90 | 90 | 70 | 95 | 30 |
| Field Bindweed | 0 | 0 | 0 | 0 | 40 | 100 | 0 | 0 | 0 | 90 | 80 | 100 | 100 | 100 | 100 | 0 | 20 | 0 | 100 | 40 | 80 | 30 | 100 | 100 | 90 | 100 | 40 | 95 | 20 |
| Morningglory | 0 | 0 | 0 | 0 | 80 | 100 | 0 | 0 | 90 | 80 | 90 | 100 | 100 | 100 | 100 | 10 | 40 | 0 | 100 | 100 | 100 | 20 | 100 | 100 | 90 | 100 | 50 | 100 | 20 |
| Velvetleaf | 0 | 0 | 0 | 0 | 100 | 100 | 0 | 0 | 90 | 100 | 100 | 100 | 100 | 100 | 100 | 100 | 100 | 100 | 100 | 100 | 95 | 100 | 100 | 100 | 100 | 100 | 100 | 100 | 100 |
| Barnyardgrass | 0 | 0 | 0 | 0 | 90 | 100 | 0 | 0 | 50 | 100 | 100 | 100 | 100 | 100 | 100 | 0 | 70 | 80 | 100 | 100 | 100 | 30 | 100 | 100 | 90 | 100 | 100 | 100 | 80 |
| Green Foxtail | 0 | 0 | 0 | 0 | 90 | 100 | 0 | 0 | 80 | 100 | 100 | 100 | 100 | 100 | 100 | 90 | 60 | 90 | 100 | 100 | 100 | 40 | 100 | 100 | 100 | 100 | 100 | 100 | 95 |
| Johnsongrass | 0 | 0 | 0 | 0 | 80 | 100 | 0 | 0 | 20 | 100 | 100 | 100 | 90 | 100 | 100 | 10 | 70 | 60 | 100 | 100 | 95 | 20 | 90 | 100 | 100 | 100 | 100 | 100 | 40 |

| Compound No. | 86 | 89 | 96 | 113 | 114 | 119 | 124 | 125 | 182 | 183 | 184 | 185 | 186 | 187 | 188 | 189 | 190 | 191 | 192 | 193 | 194 | 195 | 196 | 197 | 198 | 200 | 201 | 202 | 206 |
|---|---|---|---|---|---|---|---|---|---|---|---|---|---|---|---|---|---|---|---|---|---|---|---|---|---|---|---|---|---|
| Rate (kg/ha) | 0.125 | 0.5 | 0.5 | 8.0 | 1.0 | 0.5 | 0.5 | 1.0 | 0.5 | 0.5 | 0.5 | 0.5 | 4.0 | 4.0 | 2.0 | 1.0 | 1.0 | 8.0 | 8.0 | 8.0 | 4.0 | 0.5 | 2.0 | 4.0 | 1.0 | 1.0 | 1.0 | 1.0 | 4.0 |
| Species | % C | % C | % C | % C | % C | % C | % C | % C | % C | % C | % C | % C | % C | % C | % C | % C | % C | % C | % C | % C | % C | % C | % C | % C | % C | % C | % C | % C | % C |
| Cotton | 20 | 70 | 70 | 0 | 40 | 10 | 100 | 90 | 100 | 0 | 10 | 10 | 10 | 30 | 20 | 30 | 40 | 60 | 90 | 100 | 100 | 80 | 20 | 50 | 100 | 60 | 50 | 90 | 30 |
| Soybean | 20 | 80 | 70 | 50 | 80 | 50 | 100 | 100 | 100 | 0 | 30 | 0 | 10 | 20 | 10 | 30 | 30 | 60 | 60 | 100 | 100 | 70 | 20 | 50 | 95 | 50 | 50 | 90 | 70 |
| Field Corn | 90 | 95 | 100 | 20 | 100 | 80 | 100 | 100 | 100 | 20 | 100 | 10 | 10 | 20 | 20 | 40 | 90 | 70 | 100 | 100 | 100 | 100 | 90 | 100 | 50 | 100 | 100 | 90 | 95 |
| Wheat | 40 | 95 | 100 | 10 | 100 | 20 | 100 | 100 | 100 | 30 | 60 | 0 | 0 | 20 | 0 | 30 | 40 | 40 | 60 | 100 | 100 | 70 | 30 | 80 | 80 | 90 | 80 | 50 | 80 |
| Field Bindweed | 20 | 80 | 100 | 10 | 70 | 20 | 100 | 100 | 100 | 30 | 30 | 0 | 0 | 0 | 10 | 30 | 20 | 80 | 100 | 100 | 100 | 80 | 10 | 60 | 90 | 70 | 80 | 100 | 100 |
| Morningglory | 30 | 40 | 100 | 10 | 90 | 30 | 100 | 100 | 90 | 0 | 30 | 10 | 0 | 20 | 20 | 20 | 30 | 60 | 80 | 100 | 100 | 100 | 20 | 40 | 100 | 100 | 50 | 100 | 80 |
| Velvetleaf | 100 | 100 | 100 | 20 | 100 | 100 | 100 | 100 | 100 | 80 | 90 | 10 | 80 | 40 | 80 | 100 | 100 | 100 | 100 | 100 | 100 | 100 | 80 | 100 | 100 | 100 | 100 | 100 | 100 |
| Barnyardgrass | 95 | 95 | 100 | 60 | 100 | 40 | 100 | 100 | 100 | 80 | 90 | 20 | 20 | 10 | 0 | 100 | 100 | 100 | 100 | 100 | 100 | 100 | 100 | 50 | 100 | 100 | 100 | 100 | 80 |
| Green Foxtail | 90 | 100 | 100 | 20 | 100 | 70 | 100 | 100 | 100 | 90 | 100 | 20 | 0 | 10 | 100 | 100 | 100 | 100 | 100 | 100 | 100 | 100 | 100 | 90 | 100 | 100 | 100 | 100 | 100 |
| Johnsongrass | 60 | 100 | 90 | 30 | 100 | 70 | 100 | 100 | 100 | 90 | 90 | 0 | 0 | 10 | 30 | 90 | 100 | 100 | 100 | 100 | 100 | 90 | 90 | 90 | 95 | 100 | 90 | 90 | 100 |

| Compound No. | 207 | 208 | 209 | 210 | 211 | 212 | 213 | 214 | 215 | 218 | 219 | 220 | 221 | 222 | 223 | 224 | 225 | 226 | 227 | 228 | 229 | 230 | 231 | 232 | 233 | 234 |
|---|---|---|---|---|---|---|---|---|---|---|---|---|---|---|---|---|---|---|---|---|---|---|---|---|---|---|
| Rate (kg/ha) | 1.0 | 1.0 | 1.0 | 1.0 | 2.0 | 2.0 | 4.0 | 8.0 | 4.0 | 8.0 | 1.0 | 2.0 | 2.0 | 1.0 | 1.0 | 1.0 | 0.25 | 2.0 | 0.125 | 0.5 | 4.0 | 2.0 | 0.5 | 2.0 | 0.5 | 0.125 |
| Species | % C | % C | % C | % C | % C | % C | % C | % C | % C | % C | % C | % C | % C | % C | % C | % C | % C | % C | % C | % C | % C | % C | % C | % C | % C | % C |
| Cotton | 100 | 100 | 95 | 100 | 100 | 100 | 100 | 10 | 100 | 20 | 20 | 30 | 70 | 70 | 100 | 30 | 10 | 100 | 50 | 90 | 20 | 90 | 80 | 100 | 70 | 80 |
| Soybean | 100 | 100 | 80 | 70 | 95 | 100 | 100 | 50 | 100 | 0 | 30 | 90 | 95 | 40 | 100 | 70 | 20 | 100 | 30 | 95 | 30 | 95 | 70 | 100 | 95 | 10 |
| Field Corn | 70 | 80 | 10 | 20 | 100 | 100 | 100 | 50 | 100 | 20 | 30 | 70 | 70 | 30 | 95 | 80 | 95 | 100 | 100 | 0 | 80 | 100 | 10 | 40 | 40 | 95 |
| Wheat | 90 | 80 | 30 | 60 | 100 | 100 | 100 | 30 | 100 | 10 | 20 | 0 | 30 | 10 | 70 | 20 | 90 | 100 | 100 | 30 | 50 | 100 | 20 | 90 | 60 | 100 |
| Field Bindweed | 100 | 100 | 100 | 100 | 100 | 100 | 100 | 90 | 100 | 50 | 30 | 30 | 100 | 90 | 90 | 20 | 80 | 90 | 95 | 100 | 80 | 100 | 100 | 100 | 100 | 100 |
| Morningglory | 80 | 100 | 100 | 95 | 100 | 100 | 100 | 70 | 100 | 20 | 50 | 95 | 100 | 100 | 100 | 90 | 100 | 100 | 70 | 100 | 95 | 95 | 90 | 60 | 95 | 100 |

TABLE 3-continued

| | Preemergence Herbicidal Activity | | | | | | | | | | | | | | | | | | | | | | | | | |
|---|---|---|---|---|---|---|---|---|---|---|---|---|---|---|---|---|---|---|---|---|---|---|---|---|---|---|
| Velvetleaf | 100 | 100 | 100 | 100 | 100 | 100 | 100 | 100 | 100 | 100 | 100 | 80 | 80 | 100 | 100 | 100 | 100 | 100 | 100 | 100 | 100 | 100 | 100 | 100 | 100 | 100 |
| Barnyardgrass | 100 | 100 | 100 | 70 | 100 | 100 | 100 | 20 | 100 | 30 | 90 | 90 | 95 | 0 | 95 | 100 | 100 | 100 | 100 | 70 | 90 | 100 | 20 | 70 | 100 | 100 |
| Green Foxtail | 100 | 100 | 95 | 80 | 100 | 100 | 100 | 100 | 100 | 100 | 100 | 90 | 100 | 0 | 100 | 100 | 90 | 100 | 100 | 95 | 100 | 100 | 30 | 100 | 100 | 100 |
| Johnsongrass | 100 | 95 | 90 | 70 | 100 | 100 | 100 | 60 | 100 | 90 | 60 | 70 | 95 | 0 | 95 | 80 | 40 | 100 | 100 | 100 | 95 | 100 | 70 | 30 | 80 | 100 |

TABLE 4

Postemergence Herbicidal Activity

| Compound No. | 1 | 2 | 3 | 4 | 5 | 6 | 7 | 8 | 9 | 10 | 11 | 12 | 13 | 15 | 16 | 17 | 18 | 19 | 20 | 21 | 22 | 23 | 24 | 25 | 26 | 27 | 28 | 29 |
|---|---|---|---|---|---|---|---|---|---|---|---|---|---|---|---|---|---|---|---|---|---|---|---|---|---|---|---|---|
| Rate (kg/ha) | 8.0 | 8.0 | 8.0 | 8.0 | 8.0 | 8.0 | 8.0 | 8.0 | 8.0 | 8.0 | 8.0 | 8.0 | 4.0 | 8.0 | 8.0 | 8.0 | 8.0 | 8.0 | 8.0 | 0.25 | 8.0 | 8.0 | 0.5 | 8.0 | 8.0 | 8.0 | 8.0 | 8.0 |
| Species | % K | % C | % K | % C | % C | % C | % C | % K | % K | % K | % K | % K | % K | % K | % K | % K | % K | % K | % K | % C | % C | % C | % C | % C | % C | % C | % C | % C |
| Cotton | 0 | 30 | 100 | 0 | 20 | 60 | 100 | 0 | 0 | 20 | 0 | 100 | 70 | 95 | 20 | 0 | 100 | 100 | 100 | 100 | 100 | 80 | 100 | 30 | 90 | 100 | 80 | 100 |
| Soybean | 0 | 40 | 0 | 20 | 20 | 60 | 100 | 0 | 0 | 0 | 0 | 100 | 0 | 0 | 0 | 0 | 100 | 100 | 100 | 70 | 90 | 100 | 80 | 40 | 60 | 90 | 90 | 70 |
| Field Corn | 0 | 30 | 30 | 0 | 0 | 70 | 100 | 0 | 0 | 0 | 0 | 100 | 30 | 0 | 30 | 30 | 100 | 100 | 100 | 100 | 70 | 100 | 90 | 0 | 90 | 70 | 100 | 100 |
| Wheat | 0 | 30 | 50 | 10 | 20 | 20 | 100 | 0 | 0 | 0 | 0 | 100 | 0 | 0 | 0 | 0 | 100 | 100 | 100 | 100 | 20 | 90 | 80 | 40 | 100 | 100 | 40 | 100 |
| Field Bindweed | 0 | 40 | 100 | 0 | 0 | 30 | 100 | 0 | 0 | 0 | 10 | 100 | 70 | 0 | 70 | 70 | 100 | 100 | 100 | 100 | 90 | 50 | 100 | 0 | 60 | 100 | 50 | 100 |
| Morningglory | 0 | 40 | 100 | 0 | 0 | 30 | 100 | 0 | 0 | 20 | 0 | 100 | 20 | 60 | 10 | 10 | 100 | 100 | 100 | 100 | 90 | 70 | 100 | 10 | 50 | 80 | 80 | 100 |
| Velvetleaf | 0 | 60 | 100 | 0 | 0 | 60 | 100 | 0 | 0 | 100 | 0 | 100 | 100 | 100 | 100 | 100 | 100 | 100 | 100 | 100 | 100 | 100 | 100 | 50 | 100 | 100 | 90 | 100 |
| Barnyardgrass | 0 | 0 | 30 | 30 | 0 | 20 | 100 | 100 | 0 | 0 | 0 | 100 | 0 | 20 | 20 | 20 | 100 | 100 | 100 | 100 | 100 | 100 | 100 | 30 | 90 | 100 | 100 | 100 |
| Green Foxtail | 0 | 20 | 100 | 0 | 0 | 100 | 100 | — | 0 | 0 | 0 | 100 | — | 100 | 100 | 100 | 100 | 100 | 100 | 100 | 100 | 100 | 100 | 100 | 100 | 100 | 100 | 100 |
| Johnsongrass | 0 | 0 | 100 | 0 | 0 | 40 | 100 | 100 | 0 | 0 | 10 | 100 | 90 | 60 | 100 | 100 | 100 | 100 | 100 | 100 | 30 | 100 | 100 | 30 | 90 | 100 | 70 | 100 |

| Compound No. | 30 | 31 | 32 | 33 | 34 | 35 | 36 | 37 | 38 | 39 | 40 | 41 | 42 | 43 | 44 | 45 | 46 | 47 | 48 | 49 | 50 | 53 | 55 | 73 | 75 | 76 | 77 | 78 |
|---|---|---|---|---|---|---|---|---|---|---|---|---|---|---|---|---|---|---|---|---|---|---|---|---|---|---|---|---|
| Rate (kg/ha) | 8.0 | 8.0 | 8.0 | 8.0 | 8.0 | 8.0 | 8.0 | 8.0 | 8.0 | 8.0 | 8.0 | 0.5 | 1.0 | 1.0 | 0.5 | 4.0 | 4.0 | 4.0 | 0.25 | 2.0 | 2.0 | 0.25 | 0.5 | 4.0 | 1.0 | 1.0 | 4.0 | 1.0 |
| Species | % C | % C | % C | % C | % C | % C | % C | % C | % C | % C | % C | % C | % C | % C | % C | % C | % C | % C | % C | % C | % C | % C | % C | % C | % C | % C | % C | % C |
| Cotton | 100 | 10 | 10 | 10 | 20 | 90 | 90 | 0 | 10 | 30 | 60 | 100 | 100 | 100 | 100 | 100 | 10 | 90 | 50 | 100 | 80 | 90 | 40 | 80 | 100 | 90 | 100 | 100 |
| Soybean | 90 | 20 | 10 | 30 | 10 | 80 | 90 | 0 | 10 | 40 | 60 | 70 | 100 | 90 | 100 | 90 | 10 | 90 | 30 | 100 | 50 | 80 | 30 | 50 | 100 | 90 | 90 | 60 |
| Field Corn | 100 | 20 | 20 | 20 | 20 | 10 | 90 | 0 | 20 | 30 | 30 | 80 | 70 | 80 | 100 | 100 | 0 | 10 | 0 | 100 | 100 | 90 | 10 | 40 | 80 | 40 | 80 | 20 |
| Wheat | 80 | 20 | 10 | 20 | 20 | 30 | 30 | 0 | 10 | 30 | 30 | 70 | 100 | 20 | 100 | 100 | 0 | 10 | 0 | 10 | 70 | 40 | 20 | 80 | 70 | 30 | 50 | 40 |
| Field Bindweed | 100 | 0 | 10 | 20 | 10 | 30 | 100 | 0 | 10 | 30 | 40 | 100 | 100 | 100 | 100 | 100 | 10 | 50 | 10 | 90 | 80 | 80 | 20 | 80 | 100 | 100 | 100 | 80 |
| Morningglory | 100 | 10 | 10 | 30 | 20 | 10 | 100 | 10 | 10 | 20 | 60 | 100 | 100 | 90 | 100 | 100 | 40 | 30 | 10 | 90 | 20 | 80 | 40 | 80 | 100 | 90 | 100 | 80 |
| Velvetleaf | 100 | 0 | 10 | 20 | 20 | 100 | 100 | 0 | 0 | 60 | 80 | 100 | 100 | 100 | 100 | 100 | 0 | 90 | 90 | 100 | 100 | 100 | 80 | 100 | 100 | 100 | 100 | 100 |
| Barnyardgrass | 100 | 30 | 20 | 20 | 30 | 30 | 80 | 0 | 10 | 40 | 30 | 80 | 100 | 100 | 100 | 100 | 10 | 0 | 0 | 100 | 90 | 90 | 10 | 20 | 80 | 30 | 100 | 50 |
| Green Foxtail | 100 | 20 | 10 | 20 | 10 | 80 | 100 | 50 | 30 | 70 | 90 | 100 | 100 | 100 | 100 | 100 | 50 | 90 | 20 | 100 | 100 | 100 | 30 | 90 | 100 | 80 | 100 | 50 |
| Johnsongrass | 100 | 30 | 20 | 20 | 20 | 30 | 80 | 0 | 0 | 50 | 50 | 90 | 100 | 60 | 100 | 100 | 20 | 0 | 0 | 50 | 90 | 60 | 0 | 80 | 80 | 50 | 80 | 40 |

| Compound No. | 82 | 85 | 86 | 89 | 96 | 113 | 114 | 119 | 124 | 125 | 182 | 183 | 184 | 185 | 186 | 187 | 188 | 189 | 190 | 191 | 192 | 193 | 194 | 195 | 196 | 197 | 198 | 200 |
|---|---|---|---|---|---|---|---|---|---|---|---|---|---|---|---|---|---|---|---|---|---|---|---|---|---|---|---|---|
| Rate (kg/ha) | 2.0 | 0.5 | 0.125 | 0.5 | 0.5 | 8.0 | 1.0 | 0.5 | 4.0 | 1.0 | 0.5 | 0.5 | 0.5 | 0.5 | 4.0 | 4.0 | 2.0 | 1.0 | 1.0 | 8.0 | 8.0 | 8.0 | 4.0 | 0.5 | 2.0 | 4.0 | 1.0 | 1.0 |
| Species | % C | % C | % C | % C | % C | % C | % C | % C | % C | % C | % C | % C | % C | % C | % C | % C | % C | % C | % C | % C | % C | % C | % C | % C | % C | % C | % C | % C |
| Cotton | 95 | 95 | 95 | 80 | 100 | 0 | 100 | 70 | 100 | 100 | 100 | 80 | 90 | 30 | 30 | 30 | 30 | 80 | 80 | 80 | 90 | 100 | 100 | 70 | 90 | 90 | 100 | 100 |
| Soybean | 95 | 90 | 70 | 90 | 90 | 20 | 90 | 30 | 100 | 80 | 80 | 60 | 60 | 10 | 20 | 10 | 10 | 60 | 80 | 60 | 50 | 100 | 80 | 30 | 70 | 30 | 100 | 80 |
| Field Corn | 100 | 80 | 90 | 95 | 100 | 20 | 100 | 20 | 100 | 100 | 90 | 100 | 100 | 30 | 10 | 20 | 10 | 20 | 40 | 90 | 90 | 100 | 100 | 30 | 20 | 0 | 95 | 95 |
| Wheat | 90 | 50 | 70 | 80 | 90 | 10 | 50 | 10 | 100 | 90 | 80 | 30 | 70 | 10 | 10 | 20 | 20 | 20 | 20 | 50 | 50 | 100 | 40 | 30 | 0 | 0 | 100 | 90 |
| Field Bindweed | 100 | 95 | 95 | 70 | 100 | 10 | 100 | 70 | 100 | 100 | 100 | 30 | 80 | 10 | 20 | 0 | 30 | 30 | 50 | 30 | 30 | 100 | 90 | 50 | 60 | 0 | 100 | 100 |
| Morningglory | 90 | 80 | 100 | 60 | 100 | 10 | 100 | 40 | 100 | 100 | 100 | 40 | 70 | 30 | 0 | 0 | 10 | 70 | 90 | 70 | 100 | 100 | 100 | 80 | 30 | 0 | 100 | 100 |
| Velvetleaf | 100 | 100 | 100 | 100 | 100 | 20 | 100 | 100 | 100 | 100 | 100 | 90 | 100 | 50 | 30 | 10 | 100 | 100 | 100 | 100 | 100 | 100 | 100 | 100 | 100 | 100 | 100 | 100 |
| Barnyardgrass | 100 | 70 | 90 | 90 | 100 | 20 | 100 | 30 | 100 | 100 | 100 | 10 | 50 | 10 | 20 | 0 | 10 | 20 | 80 | 90 | 100 | 100 | 90 | 90 | 90 | 30 | 100 | 100 |
| Green Foxtail | 100 | 100 | 100 | 90 | 100 | 10 | 100 | 40 | 100 | 100 | 100 | 90 | 100 | 30 | 0 | 0 | 20 | 40 | 90 | 90 | 100 | 100 | 80 | 100 | 100 | 70 | 100 | 100 |
| Johnsongrass | 80 | 60 | 30 | 90 | 90 | 10 | 70 | 30 | 100 | 80 | 100 | 30 | 80 | 0 | 0 | 0 | 0 | 20 | 30 | 80 | 100 | 100 | 30 | 80 | 0 | 80 | 100 | 95 |

| Compound No. | 201 | 202 | 206 | 207 | 208 | 209 | 210 | 211 | 212 | 213 | 214 | 215 | 218 | 219 | 220 | 221 | 222 | 223 | 224 | 225 | 226 | 227 | 228 | 229 | 230 | 231 | 232 | 233 | 234 |
|---|---|---|---|---|---|---|---|---|---|---|---|---|---|---|---|---|---|---|---|---|---|---|---|---|---|---|---|---|---|
| Rate (kg/ha) | 1.0 | 1.0 | 4.0 | 1.0 | 1.0 | 1.0 | 1.0 | 2.0 | 2.0 | 4.0 | 8.0 | 4.0 | 8.0 | 1.0 | 2.0 | 2.0 | 1.0 | 1.0 | 1.0 | 0.25 | 2.0 | 0.125 | 0.5 | 4.0 | 2.0 | 0.5 | 2.0 | 0.5 | 0.125 |
| Species | % C | % C | % C | % C | % C | % C | % C | % C | % C | % C | % C | % C | % C | % C | % C | % C | % C | % C | % C | % C | % C | % C | % C | % C | % C | % C | % C | % C | % C |
| Cotton | 95 | 100 | 90 | 100 | 100 | 100 | 50 | 100 | 100 | 100 | 30 | 100 | 70 | 95 | 80 | 95 | 95 | 100 | 100 | 100 | 100 | 90 | 100 | 90 | 100 | 40 | 100 | 95 | 70 |
| Soybean | 70 | 90 | 80 | 100 | 100 | 90 | 20 | 95 | 100 | 100 | 50 | 100 | 60 | 60 | 100 | 95 | 80 | 100 | 80 | 80 | 95 | 60 | 100 | 60 | 100 | 80 | 100 | 95 | 60 |
| Field Corn | 100 | 100 | 100 | 50 | 20 | 20 | 10 | 100 | 100 | 100 | 80 | 100 | 30 | 70 | 90 | 95 | 40 | 40 | 40 | 60 | 100 | 90 | 30 | 30 | 100 | 0 | 100 | 40 | 80 |
| Wheat | 70 | 40 | 40 | 90 | 90 | 30 | 20 | 100 | 100 | 100 | 30 | 100 | 10 | 50 | 40 | 50 | 30 | 95 | 40 | 60 | 100 | 90 | 80 | 50 | 100 | 50 | 100 | 80 | 70 |
| Field Bindweed | 100 | 100 | 95 | 100 | 100 | 100 | 100 | 100 | 100 | 100 | 90 | 100 | 90 | 80 | 90 | 100 | 100 | 100 | 60 | 95 | 100 | 100 | 100 | 80 | 100 | 100 | 100 | 100 | 70 |
| Morningglory | 100 | 100 | 90 | 90 | 100 | 100 | 100 | 100 | 100 | 100 | 100 | 100 | 40 | 90 | 100 | 100 | 95 | 100 | 50 | 90 | 100 | 95 | 100 | 100 | 100 | 100 | 100 | 80 | 80 |

TABLE 4-continued

| | Postemergence Herbicidal Activity | | | | | | | | | | | | | | | | | | | | | | | | | | | | |
|---|---|---|---|---|---|---|---|---|---|---|---|---|---|---|---|---|---|---|---|---|---|---|---|---|---|---|---|---|---|
| Velvetleaf | 100 | 100 | 100 | 100 | 100 | 100 | 100 | 100 | 100 | 100 | 100 | 100 | 100 | 100 | 100 | 100 | 100 | 100 | 100 | 100 | 100 | 100 | 100 | 100 | 100 | 100 | 100 | 95 | 100 |
| Barnyardgrass | 95 | 100 | 95 | 100 | 100 | 100 | 95 | 100 | 100 | 100 | 60 | 100 | 0 | 70 | 100 | 100 | 0 | 100 | 10 | 60 | 100 | 100 | 100 | 90 | 100 | 20 | 100 | 100 | 80 |
| Green Foxtail | 100 | 100 | 100 | 100 | 100 | 100 | 95 | 100 | 100 | 100 | 95 | 100 | 90 | 95 | 100 | 100 | 60 | 100 | 40 | 90 | 100 | 100 | 95 | 95 | 100 | 40 | 100 | 100 | 95 |
| Johnsongrass | 40 | 80 | 100 | 80 | 70 | 70 | 60 | 100 | 100 | 100 | 80 | 100 | 0 | 30 | 50 | 100 | 0 | 100 | 10 | 40 | 100 | 95 | 95 | 70 | 95 | 10 | 100 | 30 | 40 |

I claim:

1. The compound of the formula

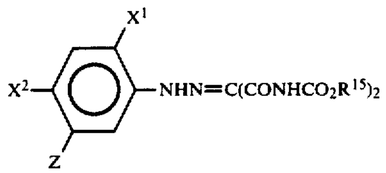

wherein $R_{15}$ is an alkyl group of 1 to 4 carbons;

$X^1$ is fluorine;

$X^2$ is chlorine or bromine;

Z is fluorine, chlorine, bromine, iodine, nitro, amino, alkoxycarbonylamino of 1 to 6 alkyl carbon atoms, di(alkylcarbonyl)amino in which each alkyl is of 1 to 6 carbon atoms, hydroxysulfonyl, halosulfonyl, alkyl of 1 to 6 carbon atoms, haloalkyl of 1 to 5 carbon atoms, —QR, —$S(O)_mR^8$, —$Q^2R^9$, Q is O R is hydrogen, alkyl of 1 to 6 carbon atoms (which is unsubstituted or substituted with cycloalkyl of 3 to 7 carbon atoms), cycloalkyl of 3 to 7 carbon atoms (which is unsubstituted or substituted with alkyl of 1 to 6 carbon atoms), benzyl, alkoxyalkyl of 2 to 8 carbon atoms, alkoxyalkoxyalkyl of 3 to 8 carbon atoms, alkylthioalkyl, alkylsulfinylalkyl, or alkylsulfonylalkyl of 2 to 8 carbon atoms, alkyenyl or haloalkenyl of 2 to 5 carbon atoms, alkynyl or haloalkynyl of 2 to 5 carbon atoms, haloalkyl of 1 to 5 carbon atoms, alkylcarbonyl of 1 to 6 alkyl carbon atoms, or dialkylaminocarbonyl or dialkylaminothiocarbonyl in which each alkyl is of 1 to 6 carbon atoms.

2. The compound of claim 1 wherein $R^{15}$ is alkyl of 1 to 4 carbon atoms and Z is fluorine, chlorine, bromine, iodine, nitro, amino, hydroxysulfonyl, chlorosulfonyl, or a group —OR in which R is alkyl of 1 to 6 carbon atoms, benzyl, alkoxyalkyl of 2 to 4 carbon atoms, or alkenyl or alkynyl of 2 to 5 carbon atoms.

3. The compound of claim 2 wherein Z is nitro, or the group —OR.

4. The compound of claim 3 wherein Z is the group —OR and R is alkyl of 1 to 4 carbon atoms.

* * * * *